Figure 4:
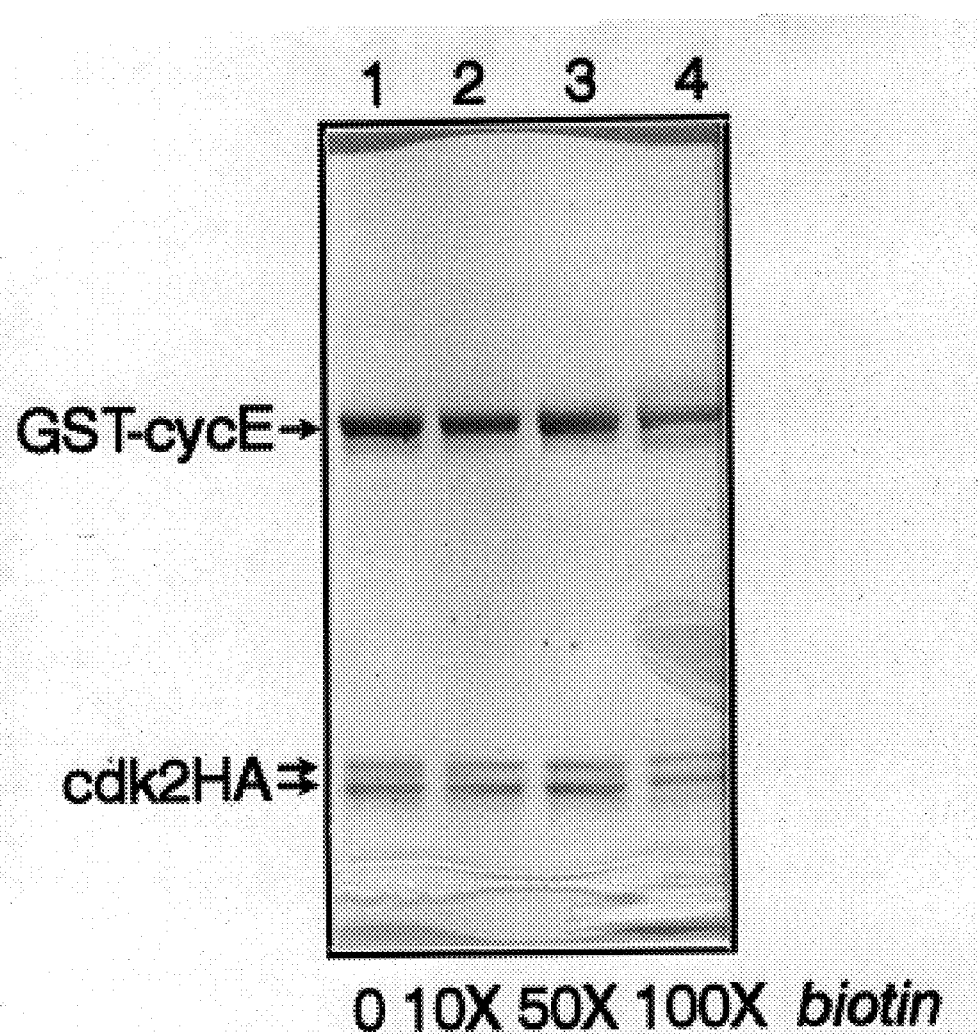

United States Patent [19]

Hollingsworth

[11] Patent Number: 6,077,700
[45] Date of Patent: Jun. 20, 2000

[54] FUSION PROTEINS OF MUTANTS OF CYCLINE E AND THEIR COMPLEXES WITH CYCLINE DEPENDENT PROTEIN KINASE

[75] Inventor: Robert E. Hollingsworth, Kalamazoo, Mich.

[73] Assignee: Pharmacia & Upjohn Company, Kalamazoo, Mich.

[21] Appl. No.: 08/895,707

[22] Filed: Jul. 17, 1997

Related U.S. Application Data

[60] Provisional application No. 60/022,338, Jul. 24, 1996.
[51] Int. Cl.⁷ .............................. C12N 9/12; C07K 14/00
[52] U.S. Cl. ............................................ 435/194; 530/350
[58] Field of Search ........................... 530/350; 536/23.5, 536/23.1; 435/69.1, 252.3, 252.33, 325, 192, 194

[56] References Cited

U.S. PATENT DOCUMENTS 5,449,755  9/1995  Roberts et al. ......................... 530/350

FOREIGN PATENT DOCUMENTS 0 646 646  4/1995  European Pat. Off. .
WO 93/06123  4/1993  WIPO .
WO 95/09239  4/1995  WIPO .

OTHER PUBLICATIONS

*J. Chromatography*, 411, pp. 177–184 (1987).
*Protein Engineering*, 6, pp. 109–122 (1993).
*J. Chromatography*, 676, pp. 337–345 (1994).
*Cell*, 78, pp. 59–66 (1994).
*Cell*, 66, 1217–1228 (1991).
*Cell*, 66, pp. 1197–1206 (1991).
*Science*, 234, pp. 364–368 (1986).
*Gene*, 67, 1, pp. 31–40 (1988).
*Bio/technology*, 11, pp. 933–936 (1993).
*Mol. Cell Biol*, 14, (12) pp. 7953–7966 (1994).
Ford et al. "Fusion tails for the recovery and purification of recombinant proteins" Prot. Express. Purif. 2, 95–107, 1991.

*Primary Examiner*—Ponnathapura Achutamurthy
*Assistant Examiner*—Nashaat T. Nashed
*Attorney, Agent, or Firm*—Nikaido Marmelstein Murray & Oram, LLP.

[57] ABSTRACT

A polypeptide of the amino acid sequence of SEQ ID NO: 2, and a composition including the polypeptide of SEQ ID NO: 2 bound to cyclin-dependent kinase 2 (Cdk2).

2 Claims, 17 Drawing Sheets

FIG. 1A

```
   1  ATGTCCCCTA TACTAGGTTA TTGGAAAATT AAGGGCCTTG TGCAACCCAC
  51  TCGACTTCTT TTGGAATATC TTGAAGAAAA ATATGAAGAG CATTTGTATG
 101  AGCGCGATGA AGGTGATAAA TGGCGAAACA AAAGTTTGA ATTGGGTTTG
 151  GAGTTTCCCA ATCTTCCTTA TTATATTGAT GGTGATGTTA AATTAACACA
 201  GTCTATGGCC ATCATACGTT ATATAGCTGA CAAGCACAAC ATGTTGGGTG
 251  GTTGTCCAAA AGAGCGTGCA GAGATTTCAA TGCTTGAAGG AGCGGTTTTG
 301  GATATTAGAT ACGGTGTTTC GAGAATTGCA TATAGTAAAG ACTTTGAAAC
 351  TCTCAAAGTT GATTTTCTTA GCAAGCTACC TGAAATGCTG AAAATGTTCG
 401  AAGATCGTTT ATGTCATAAA ACATATTTAA ATGGTGATCA TGTAACCCAT
 451  CCTGACTTCA TGTTGTATGA CGCTCTTGAT GTTGTTTTAT ACATGGACCC
 501  AATGTGCCTG GATGCGTTCC CAAAATTAGT TTGTTTTAAA AAACGTATTG
 551  AAGCTATCCC ACAAATTGAT AAGTACTTGA ATCCAGCAA GTATATAGCA
 601  TGGCCTTTGC AGGGCTGGCA AGCCACGTTT GGTGGTGTCG ACCATCCTCC
 651  AAAATCGGAT CTCATGAAGG AGGACGGCGG CGCGGAGTTC TCGGCTCGCT
 701  CCAGGAAGAG GAAGGCAAAC GTGACCGTTT TTTTGCAGGA TCCAGATGAA
 751  GAAATGGCCA AAATCGACAG GACGGCGAGG GACCAGTGTG GGAGCCAGCC
 801  TTGGGACAAT AATGCAGTCT GTGCAGACCC CTGCTCCCTG ATCCCCACAC
 851  CTGACAAAGA AGATGATGAC CGGGTTTACC CAAACTCAAC GTGCAAGCCT
 901  CGGATTATTG CACCATCCAG AGGCTCCCCG CTGCCTGTAC TGAGCTGGGC
 951  AAATAGAGAG GAAGTCTGGA AAATCATGTT AAACAAGGAA AAGACATACT
1001  TAAGGGATCA GCACTTTCTT GAGCAACACC CTCTTCTGCA GCCAAAAATG
1051  CGAGCAATTC TTCTGGATTG GTTAATGGAG GTGTGTGAAG TCTATAAACT
1101  TCACAGGGAG ACCTTTTACT TGGCACAAGA TTTCTTTGAC CGGTATATGG
1151  CGACACAAGA AAATGTTGTA AAAACTCTTT TACAGCTTAT TGGGATTTCA
1201  TCTTTATTTA TTGCAGCCAA ACTTGAGGAA ATCTATCCTC AAAGTTGCA
1251  CCAGTTTGCG TATGTGACAG ATGGAGCTTG TTCAGGAGAT GAAATTCTCA
1301  CCATGGAATT AATGATTATG AAGGCCCTTA AGTGGCGTTT AAGTCCCCTG
1351  ACTATTGTGT CCTGGCTGAA TGTATACATG CAGGTTGCAT ATCTAAATGA
1401  CTTACATGAA GTGCTACTGC CGCAGTATCC CCAGCAAATC TTTATACAGA
1451  TTGCAGAGCT GTTGGATCTC TGTGTCCTGG ATGTTGACTG CCTTGAATTT
```

FIG. 1B

```
1401  CTTACATGAA GTGCTACTGC CGCAGTATCC CCAGCAAATC TTTATACAGA
1451  TTGCAGAGCT GTTGGATCTC TGTGTCCTGG ATGTTGACTG CCTTGAATTT
1501  CCTTATGGTA TACTTGCTGC TTCGGCCTTG TATCATTTCT CGTCATCTGA
1551  ATTGATGCAA AAGGTTTCAG GGTATCAGTG GTGCGACATA GAGAACTGTG
1601  TCAAGTGGAT GGTTCCATTT GCCATGGTTA TAAGGGAGAC GGGGAGCTCA
1651  AAACTGAAGC ACTTCAGGGG CGTCGCTGAT GAAGATGCAC ACAACATACA
1701  GACCCACAGA GACAGCTTGG ATTTGCTGGA CAAAGCCCGA GCAAAGAAAG
1751  CCATGTTGTC TGAACAAAAT AGGGCTTCTC CTCTCCCCAG TGGGCTCCTC
1801  ATCGCGGCAC AGGGCGGTAA GAAGCAGAGC CACCACCACC ACCACCACTG
1851  A
```

FIGURE 2

```
            10                    30                    50
MSPILGYWKIKGLVQPTRLLLEYLEEKYEEHLYERDEGDKWRNKKFELGLEFPNLPYYID 70                    90                   110
GDVKLTQSMAIIRYIADKHNMLGGCPKERAEISMLEGAVLDIRYGVSRIAYSKDFETLKV 130                   150                   170
DFLSKLPEMLKMFEDRLCHKTYLNGDHVTHPDFMLYDALDVVLYMDPMCLDAFPKLVCFK 190                   210                   230
KRIEAIPQIDKYLKSSKYIAWPLQGWQATFGGVDHPPKSDLMKEDGGAEFSARSRKRKAN 250                   270                   290
VTVFLQDPDEEMAKIDRTARDQCGSQPWDNNAVCADPCSLIPTPDKEDDDRVYPNSTCKP 310                   330                   350
RIIAPSRGSPLPVLSWANREEVWKIMLNKEKTYLRDQHFLEQHPLLQPKMRAILLDWLME 370                   390                   410
VCEVYKLHRETFYLAQDFFDRYMATQENVVKTLLQLIGISSLFIAAKLEEIYPPKLHQFA 430                   450                   470
YVTDGACSGDEILTMELMIMKALKWRLSPLTIVSWLNVYMQVAYLNDLHEVLLPQYPQQI 490                   510                   530
FIQIAELLDLCVLDVDCLEFPYGILAASALYHFSSSELMQKVSGYQWCDIENCVKWMVPF 550                   570                   590
AMVIRETGSSKLKHFRGVADEDAHNIQTHRDSLDLLDKARAKKAMLSEQNRASPLPSGLL

610
IAAQGGKKQSHHHHHH*
```

FIGURE 3

```
 370... Arg Ala Ser Pro Leu Pro Ser Gly Leu Leu Thr Pro Pro
1108... AGG GCT TCT CCT CTC CCC AGT GGG CTC CTC ACC CCG CCA
------------------------------------------------------------

1108... AGG GCT TCT CCT CTC CCC AGT GGG CTC CTC ATC GCG GCA
 370... Arg Ala Ser Pro Leu Pro Ser Gly Leu Leu Ile Ala Ala
```

Sequences from above contined below.

```
 383... Gln Ser Gly Lys Lys Gln Ser Ser Gly Pro Glu Met Ala End
1147... CAG AGC GGT AAG AAG CAG AGC AGC GGG CCG GAA ATG GCG TGA
------------------------------------------------------------

1147... CAG GGC GGT AAG AAG CAG AGC CAC CAC CAC CAC CAC CAC TGA
 383... Gln Gly Gly Lys Lys Gln Ser His His His His His His End
```

FIGURE 8

```
85      GAAGAAATG 93
94      GCCAAAATCG ACAGGACGGC GAGGGACCAG TGTGGGAGCC AGCCTTGGGA
144     CAATAATGCA GTCTGTGCAG ACCCCTGCTC CCTGATCCCC ACACCTGACA
194     AAGAAGATGA TGACCGGGTT TACCCAAACT CAACGTGCAA GCCTCGGATT
244     ATTGCACCAT CCAGAGGCTC CCCGCTGCCT GTACTGAGCT GGGCAAATAG
294     AGAGGAAGTC TGGAAAATCA TGTTAAACAA GGAAAAGACA TACTTAAGGG
344     ATCAGCACTT TCTTGAGCAA CACCCTCTTC TGCAGCCAAA AATGCGAGCA
394     ATTCTTCTGG ATTGGTTAAT GGAGGTGTGT GAAGTCTATA AACTTCACAG
444     GGAGACCTTT TACTTGGCAC AAGATTTCTT TGACCGGTAT ATGGCGACAC
494     AAGAAAATGT TGTAAAAACT CTTTTACAGC TTATTGGGAT TTCATCTTTA
544     TTTATTGCAG CCAAACTTGA GGAAATCTAT CCTCCAAAGT TGCACCAGTT
594     TGCGTATGTG ACAGATGGAG CTTGTTCAGG AGATGAAATT CTCACCATGG
644     AATTAATGAT TATGAAGGCC CTTAAGTGGC GTTTAAGTCC CCTGACTATT
694     GTGTCCTGGC TGAATGTATA CATGCAGGTT GCATATCTAA ATGACTTACA
744     TGAAGTGCTA CTGCCGCAGT ATCCCCAGCA AATCTTTATA CAGATTGCAG
794     AGCTGTTGGA TCTCTGTGTC CTGGATGTTG ACTGCCTTGA ATTTCCTTAT
844     GGTATACTTG CTGCTTCGGC CTTGTATCAT TTCTCGTCAT CTGAATTGAT
894     GCAAAAGGTT TCAGGGTATC AGTGGTGCGA CATAGAGAAC TGTGTCAAGT
944     GGATGGTTCC ATTTGCCATG GTTATAAGGG AGACGGGGAG CTCAAAACTG
994     AAGCACTTCA GGGGCGTCGC TGATGAAGAT GCACACAACA TACAGACCCA
1044    CAGAGACAGC TTGGATTTGC TGGACAAAGC CCGAGCAAAG AAAGCCATGT
1094    TGTCTGAACA AAATAGGGCT TCTCCTCTCC CCAGTGGGCT CCTCACCCCG
1144    CCACAGAGCG GTAAG*AAGCA GAGCAGCGGG CCGGAAATGG CG 1185
```

FIGURE 9

```
 29      EE MAKIDRTARD QCGSQPWDNN
 51  AVCADPCSLI PTPDKEDDDR VYPNSTCKPR IIAPSRGSPL PVLSWANREE
101  VWKIMLNKEK TYLRDQHFLE QHPLLQPKMR AILLDWLMEV CEVYKLHRET
151  FYLAQDFFDR YMATQENVVK TLLQLIGISS LFIAAKLEEI YPPKLHQFAY
201  VTDGACSGDE ILTMELMIMK ALKWRLSPLT IVSWLNVYMQ VAYLNDLHEV
251  LLPQYPQQIF IQIAELLDLC VLDVDCLEFP YGILAASALY HFSSSELMQK
301  VSGYQWCDIE NCVKWMVPFA MVIRETGSSK LKHFRGVADE DAHNIQTHRD
351  SLDLLDKARA KKAMLSEQNR ASPLPSGLLT PPQSGKKQSS GPEMA 395
```

FUSION PROTEINS OF MUTANTS OF CYCLINE E AND THEIR COMPLEXES WITH CYCLINE DEPENDENT PROTEIN KINASE

CROSS-REFERENCE TO RELATED APPLICATIONS

This application claims the benefit of U.S. provisional application Ser. No. 60/022,338 filed Jul. 24, 1996 under 35 USC §119(e)(i).

FIELD OF THE INVENTION

This invention relates to field of kinases and cyclins, specifically, cyclin E and its complexes with cdk 2. Kinases are important enzymes involved in regulating the cell cycle.

BACKGROUND

The cell cycle is usually divided into four phases: DNA synthesis (S phase) and mitosis (M phase) separated by gaps called G1 and G2. The cell cycle is coordinated by several Ser/Thr protein kinases that are activated in a regulated manner. It is this progressive activation and inactivation of a family of Cyclin-dependent kinases (Cdk's) that regulates the cell cycle. This enzyme engine is subject to careful control in order to ensure that each event (DNA replication, nuclear envelope breakdown, spindle formation, and chromosome segregation etc) is performed correctly and in proper sequence.

Each protein kinase consists of a catalytic cyclin-dependent kinase (Cdk) subunit and a regulatory cyclin subunit. Cdks are proteins that contain the catalytic subunit (~34 kDa) and are inactive as monomers. The best characterized Cdk's, in terms of their temporal activation and cognate cyclins, are: Cdc2, Cdk2, Cdk4, and Cdk6.

Cdk activation requires their specific association with the regulatory subunits called cyclins. In human cells different types of cyclins have been idenitfied and these include types A, B, C, D, and E. Cyclins may be further grouped into "Mitotic Cyclins," which include cyclins A and B and "G1 Cyclins" which include cyclins C, D, and E. The cyclins D, E, A, and B are required in G1, G1/S, S, and G2/M phases of the cell cycle, respectively.

Cdk activation requires both cyclin binding and phosphorylation by a Cdk-activating kinase (CAK) on Thr161 of the Cdk catalytic domain. Negative regulation of Cdk is carried out through phosphorylation of Thr14 and Tyr15. The phosphorylation and dephosphorylation at these residues is mediated by several enzymes including the Wee1 kinase and Cdc25 phosphatase.

Inactivation of the cyclin-dependent kinases (Cdks) is potentially a promising route to cancer therapy and has been the subject of immense interest for the last few years. These kinases belong to a family of enzymes involved in the the events that control the eukaryotic cell cycle.

Cdc2 and Cdk2 are two particularly well understood Cdks. The major partner for Cdc2 in the cell is cyclin B. Cyclin B levels peak at the G2/M transition and the protein is involved in the induction of mitosis. Cdk2 is active in late G1 and remains active until the end of G2. The levels of cyclin E peak around the G1/S transition during the cell cycle.

The dimunition of cyclin protein levels is an important aspect of the regulation of the cell cycle in normal cells. This reduction is thought to occur by targeted protein degradation. Indeed, most of the known cyclins contain one or the other of two classes of putative degradation motifs. These motifs are regions of the proteins containing a defined amino acid sequence. Mitotic cyclins, which include cyclins A, and B, contain a so-called "destruction box," whereas G1 cyclins, which include cyclins C, D and E, contain potential "PEST" motifs.

The PEST motif is a stretch of amino acids having a specific composition, and its presence in some proteins is known to cause the rapid degradation of eukaryotic cells. The mutation of these motifs in a cyclin would thus result in the abnormal persistance of high levels of cyclin, and this may contribute to tumorigenesis.

Protein inhibitors of Cdk/cyclin complexes mediating cell cycle progression have been discovered. The mammalian Cdk protein inhibitors fall into two categories based on sequence homology. One class is related to p16, and includes specific inhibitors of Cdk4 and Cdk6. The other class, related to p21, includes p21, p27 and p57.

The inhibitors related to p21 are known as the cyclin-dependent kinase inhibitory proteins (Kips). "Kips" used without a specific number identification usually refer to a family of proteins. Some proteins within that family may be given a more specific "name" that includes the letters kip or even cip, such as, p27-KIP1 or p21-CIP1. Capitalization may vary, e.g. kip, Kip, KIP or cip, Cip, CIP. Kips inhibit a wide variety of complexes including Cdk4/Cdk6-cyclin D, Cdk2-Cyclin A/Cyclin E, and cdc2/cyclin B. Human p21 (Cipl) encodes a protein of 164 amino acids and human p27 (Kip1) encodes a protein of 198 amino acids.

The Cdk2/cyclin E complex and associated cell cycle regulatory functions is an important research area and the search for inhibitors of this complex is an important research goal. If soluble, active complexes of Cdk2/cyclin E could be created, they would fill a critical need for a tool to create in vitro screens designed to detect inhibitors of the kinase activity of this complex and they might facilitate studies designed to characterize the complex and elucidate its properties.

The invention disclosed herein discloses various forms of cyclin E that create such soluble and active Cdk2/cyclin E complexs.

BRIEF DESCRIPTION OF THE DRAWINGS AND FIGURES

FIGS. 1A and 1B DNA sequence encoding GST-cyclin E-PEST*-His6 gene. Note that sequence numbering differs from that used in FIG. 2 of Koff et al (1991) *Cell* 66:1217–1228. This is SEQ. ID. NO. 1.

FIG. 2. Amino acid sequence of the GST-cyclin E-PEST*-His6. This is SEQ. ID. NO. 2.

FIG. 3. Comparison of the C-termini of GST-cyclin E-PEST*-His6 and wild type cyclin E. Above the dotted lines, wild type cyclin E; and below the dotted lines, GST-cyclin E-PEST*-His6. Numbering is the same as used in FIG. 2 of Koff et al (1991) *Cell* 66:1217–1228 for wild type cyclin E. Differences in the GST-cyclin E-PEST*-His6 from the wild type are indicated by bold type. The putative PEST region of wild type cyclin E is underlined. (The portion of full length wild type amino acid shown is provided in SEQ. ID. NO. 3, and the full length wild type DNA corresponding to SEQ. ID. NO. 3, is provided in SEQ. ID. NO. 4. The full length GST-cyclin E-PEST*-His6, which includes the C-terminus is shown in FIG. 3, is provided as SEQ. ID. NOs. 1 and 2.

FIG. 4. Affinity purified GST-cyclin E-PEST*-His6/cdk2 complexes. Protein preparations were visualized by SDS-polyacrylamide gel electrophoresis and Coomassie staining. Lane 1, GST-cyclin E (wild type)/cdk2-HA purified by glutathione affinity chromatography. Lane 2, GST-cyclin E-PEST*-His6/cdk2-HA purified by glutathione affinity chromatography. Lane 3, GST-cyclin E-PEST*-His6/cdk2-HA purified by immobilized metal affinity chromatography (IMAC). Lane 4, GST-cyclin E-PEST*-His6/cdk2-HA purified by glutathione affinity chromatography and biotinylated with NHS-LC-biotin (Pierce). The markers to the left of the Figure, "GST-cycE" and "cdk2HA" show the expected position of the various GST-cyclin E and cdk2-HA species.

Figure 5:
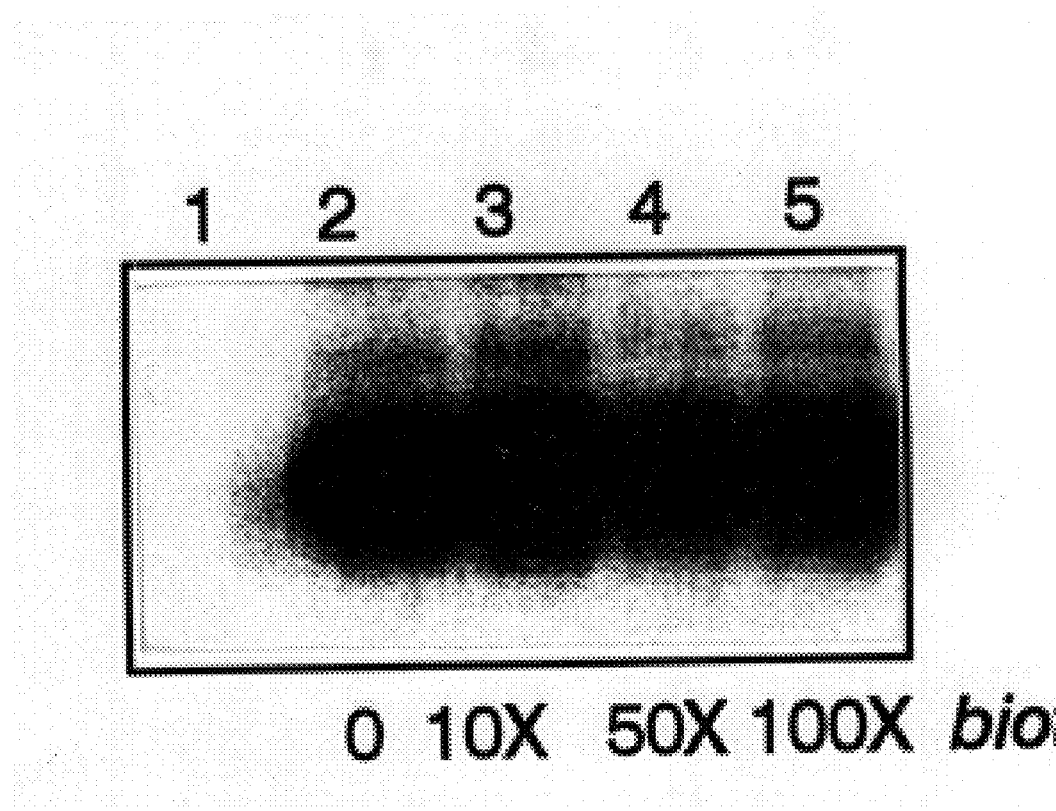

FIG. 5. Kinase activity of GST-cyclin E-PEST*-His6/cdk2 complexes. Kinase assays were performed by incubating cyclin E/cdk2 complexes in 50 mM Tris-HCl pH 7.4, 10 mM MgCl$_2$, 1 mM DTT, 0.2 mM ATP, 0.25 mCi/ml [$\gamma^{32}$P]-ATP and 10 ng/$\mu$l purified RB protein (QED, Inc., San Diego). Reaction products were then analyzed by SDS-polyacrylamide gel electrophoresis and PhosphorImaging. Lane 1, purified cdk2-HA only. Lane 2, GST-cyclin E (wild type)/cdk2-HA purified by glutathione affinity chromatography. Lane 3, GST-cyclin E-PEST*-His6/cdk2-HA purified by glutathione affinity chromatography. Lane 4, GST-cyclin E-PEST*-His6/cdk2-HA purified by immobilized metal affinity chromatography (IMAC). Lane 5, GST-cyclin E-PEST*-His6/cdk2-HA purified by glutathione affinity chromatography and biotinylated with NHS-LC-biotin.

Figure 6:
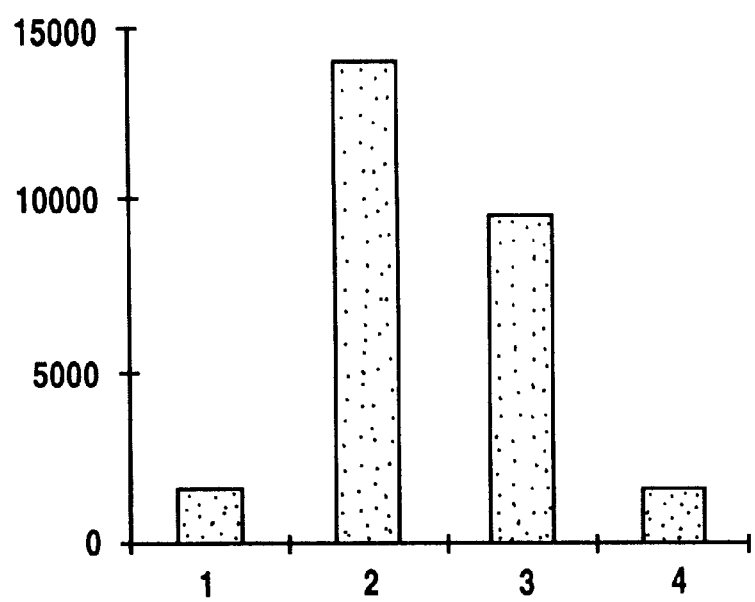

FIG. 6. Binding of Kinase Inhibitor Proteins (p27$^{KIP1}$) to GST-cyclin E-PEST*-His6/cdk2 complexes. The Y-axis (cpm) is counts per minute and the X-axis (r) is the Reaction number. KIP scintillation proximity assays were performed as described below. Reaction 1, background ($^3$H-mini-p27, such as the minimal domains disclosed in Polyak, et al., *Cell* (1994) Vol. 78, pp. 59–66, or $^{125}$1I-GST-p21+SPA beads, no cyclin E/cdk2 complex present). The $^{125}$1I-GST-p21 construct is the radioactive $^{125}$I-form of a p21 construct. For preparations of non-radioactive constructs otherwise similar to $^{125}$I-GST-p21, see El-Deiry et al., "WAFI, a Potential Mediator of p53 Tumor Suppression," *Cell* (1993) Vol. 75, pp. 817–825. Reaction 2, $^{25}$1I-GST-p21+GST-cyclin E-PEST*-His6/cdk2 complex; reaction 3, $^3$H-mini-p27+GST-cyclin E-PEST*-His6/cdk2 complex. Reaction 4, $^3$H-mini-p27+excess mini-p27+GST-cyclin E-PEST*-His6/cdk2 complex (cold competition).

Figure 7:
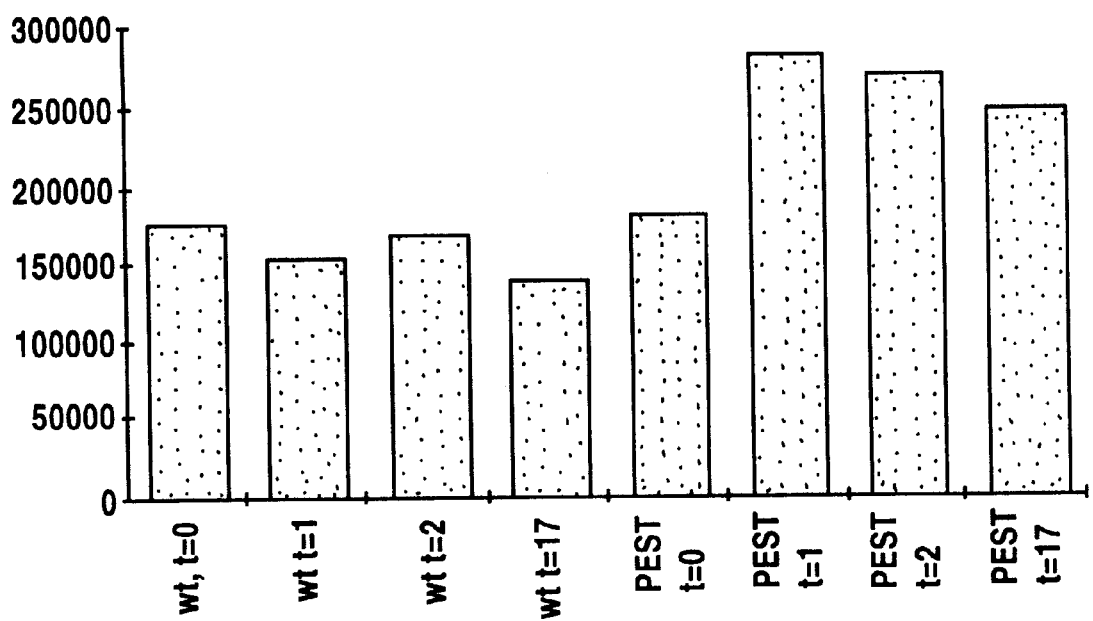

FIG. 7. Stability of GST-cyclin E-PEST*-His6 vs. wild type GST-cyclin E in insect cells. Sf 9 insect cells were infected with recombinant baculoviruses encoding either GST-cyclin E-PEST*-His6 or wild type GST-cyclin E. The Y-axis (v) is the volume integration of radioactive signal and the X-axis (s) is sample type. Infected cells were pulsed for 2 hours with $^{35}$S-amino acids and then chased with cold amino acids. At the indicated time points (time 0=end of pulse), cells were harvested and proteins analyzed by SDS-polyacrylamide gel electrophoresis and PhosphorImaging®. Histograms represent volume integration of radioactive signal within bands corresponding to GST-cyclin E species. "wt," indicates GST-cyclin E (wild type); "PEST," indicates GST-cyclin E-PEST*-His6.

FIG. 8. DNA sequence of special cyclin E (29E-395A). This is SEQ. ID. NO. 5.

FIG. 9. Amino acid sequence of special cyclin E (29E-395A). This SEQ. ID. NO. 6.

Figure 10:
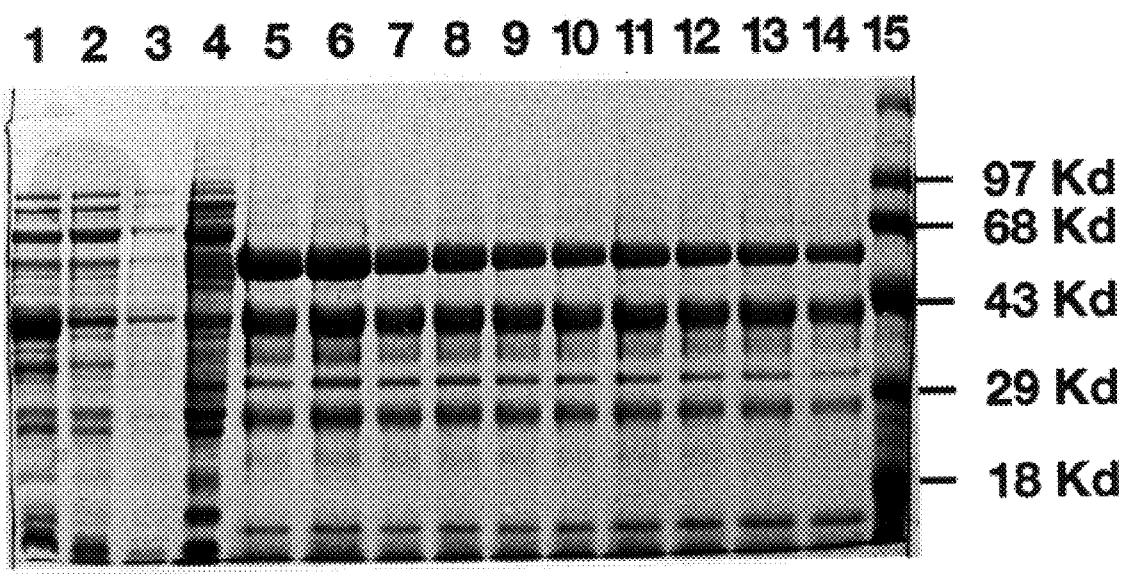

FIG. 10. IMAC purification of special cyclin E (MRHHHHHHK)-(29E-395A)-(SAWRHPQFGG) (SEQ. ID. NO. 7) in the presence of NaCl which favors the association with GroEL. SEQ. ID. NO. 8, lists the DNA sequence that corresponds to the amino acid sequence of SEQ. ID. NO. 7. SEQ. ID. NO. 9, lists the amino acid sequence of (MRHHHHHHK). SEQ. ID. NO. 10, lists the DNA sequence that corresponds to the amino acid sequence of SEQ. ID. NO. 9. SEQ. ID. NO. 11, lists the amino acid sequence of (SAWRHPQFGG). SEQ. ID. NO. 12, lists the DNA sequence that corresponds to the amino acid sequence of SEQ. ID. NO. 11. The cell pellets are resuspended in 20 mM Tris, pH 8.0, 0.5 M NaCl, processed using a French Pressure Cell and the extract centrifuged. The supernatant is then loaded onto an IMAC column equilibrated in 20 mM Tris, pH 8.0, 0.5 M NaCl. The column is washed with 20 mM Tris, pH 8.0, 0.5 M NaCl followed by buffer plus 75 mM imidazole. The special cyclin E (29E-395A)/GroEL complex is eluted using buffer plus 300 mM imidazole and fractions are collected and analyzed using 12% SDS-PAGE. Lane 1, total cell lysate after processing with French Press; Lane 2, supernatant loaded onto IMAC; Lane 3, IMAC flow through material; Lane 4, 75 mM imidazole wash; Lanes 5–14, fractions from 300 mM imidazole elution of cyclin E (29E-395A); Lane 15, MW marker. The major protein band between 43 Kd and 68 Kd was identified to be GroEL. The major protein band slightly below the 43 Kd band was identified to be special cyclin E (MRHHHHHHK)-(29E-395A)-(SAWRHPQFGG), SEQ. ID. NO. 7.

Figure 11:
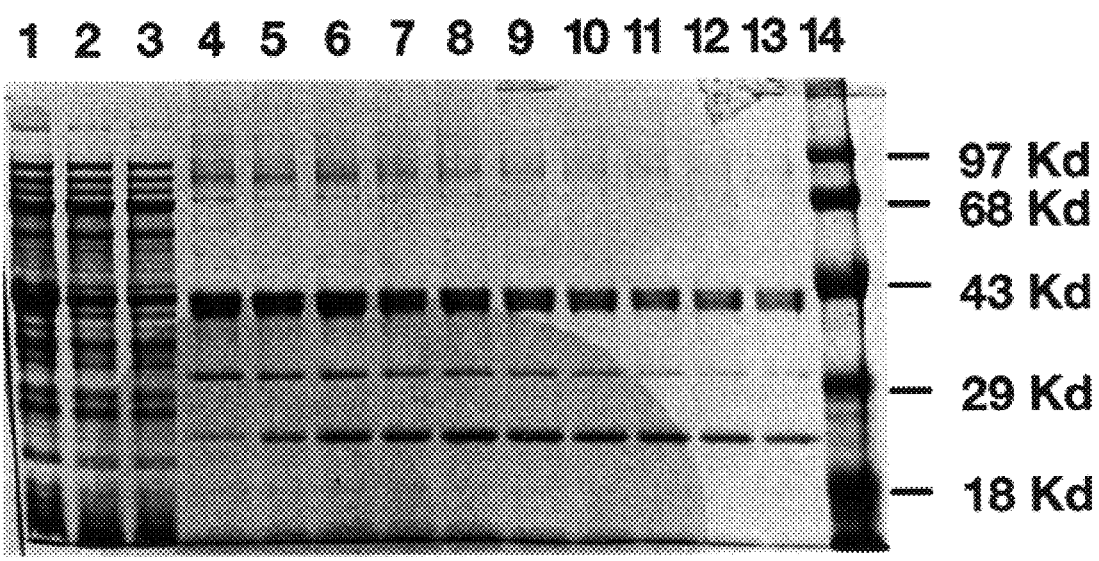

FIG. 11. IMAC purification of special cyclin E (MRHHHHHHK)-(29E-395A)-(SAWRHPQFGG), SEQ. ID. NO. 7, in the absence of NaCl which favors the dissociation with GroEL. The cyclin E (29E-395A) clone is grown and expressed as before. The cell pellets are resuspended in 50 mM Tris, pH 8.0, processed using a French Pressure Cell and the extract centrifuged. The supernatant is then loaded onto an IMAC column equilibrated in 50 mM Tris, pH 8.0. The column is washed with 50 mM Tris, pH 8.0, followed by buffer plus 75 mM imidazole. The cyclin E (29E-395A) is eluted using buffer plus 300 mM imidazole. The cyclin E thus eluted was insoluble and cyclin E containing fractions are collected and analyzed using 12% SDS-PAGE. Lane 1, total cell lysate after processing with French Press; Lane 2, supernatant loaded onto IMAC; Lane 3, IMAC flow through material; Lanes 4–13, fractions from 300 mM imidazole elution of cyclin E (29E-395A); Lane 15, MW marker. Notably, the GroEL band between 43 Kd and 68 Kd is not observed.

Figure 12:
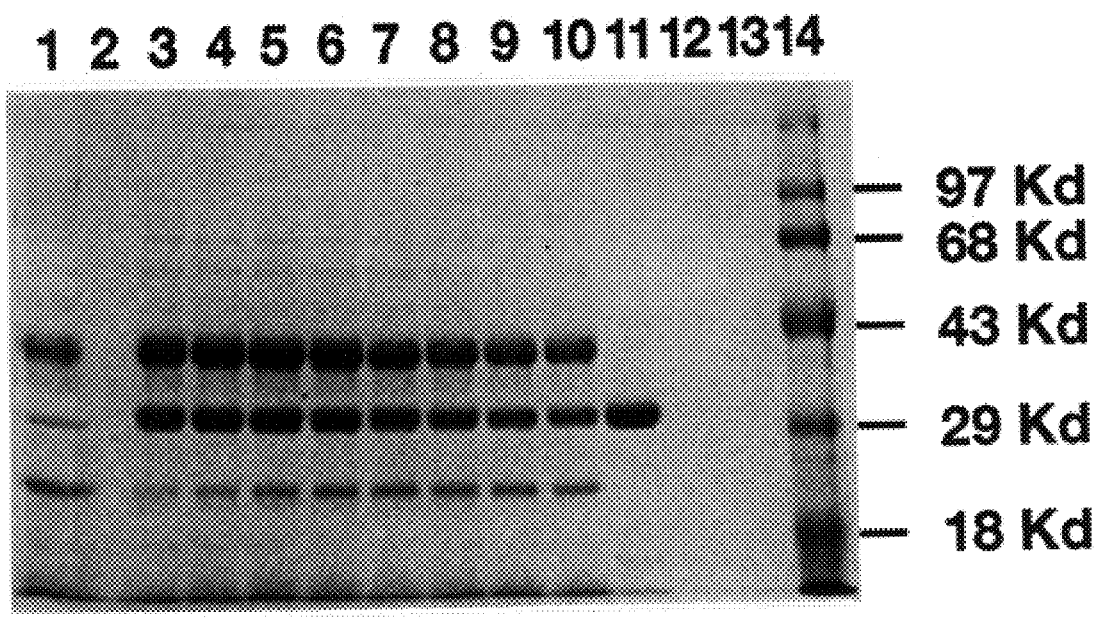

FIG. 12. IMAC purification of human cyclin E (MRHHHHHHK)-(29E-395A)-(SAWRHPQFGG)/cdk2 complex (SEQ. ID. NO. 7/cdk2 complex). The cell pellets are resuspended in 50 mM Tris, pH 8.0, processed using a French Pressure Cell and the extract centrifuged. The supernatant is then loaded onto an IMAC column equilibrated in 50 mM Tris, pH 8.0. The column is washed with 50 mM Tris, pH 8.0, followed by buffer plus 50 mM imidazole. Cdk2 is equilibrated to 50 mM imidazole and loaded onto the column. The column is washed with 50 mM imidazole followed by 75 mM imidazole until the absorbance is approximately 0.25 A$_{280}$. The cyclin E (29E-395A)/cdk2 complex is eluted using buffer plus 300 mM imidazole and fractions are collected and analyzed using 12% SDS-PAGE. Lane 1, IMAC purified cyclin E (29E-395A) isolated in the absence of NaCl; Lanes 3–10, fractions from 300 mM imidazole elution of cyclin E (29E-395A)/cdk2 complex; Lane 11, cdk2; Lane 14, MW markers.

Figure 13:
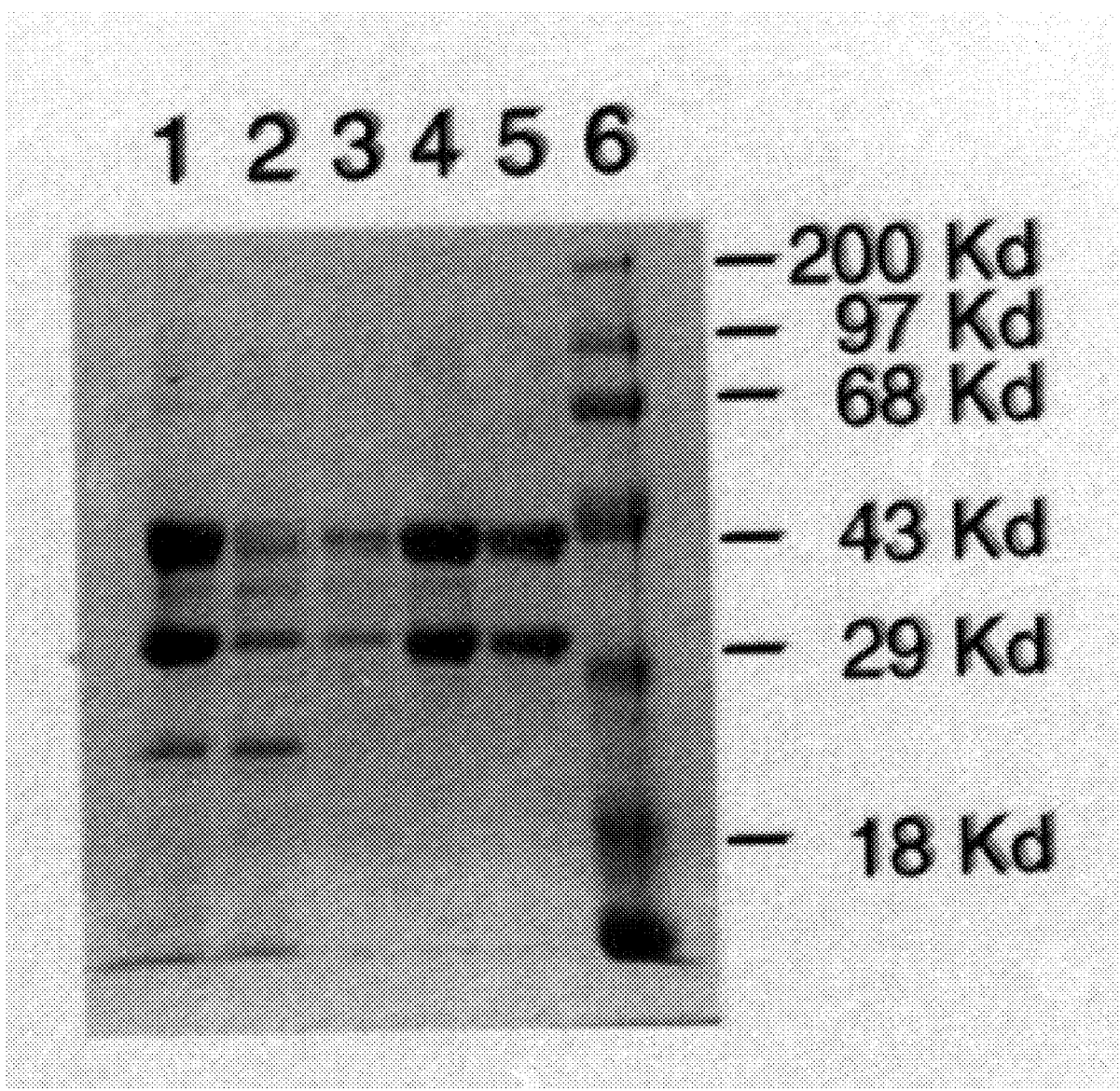

FIG. 13. Purification of (MRHHHHHHK)-(29E-395A)-(SAWRHPQFGG)/cdk2 complex (SEQ. ID. NO. 7/cdk2 complex) using immobilized streptavidin. SDS-PAGE (12%) of (MRHHHHHHK)-(29E-395A)-(SAWRHPQFGG)/cdk2 complex (SEQ. ID. NO. 7/cdk2 complex) purified by using immobilized streptavidin. Lane 1 IMAC purified complex; Lane 2, unbound fraction, Lanes 3–5, fractions eluted with 10 mM biotin; Lane 6, molecular weight markers.

Figure 14:
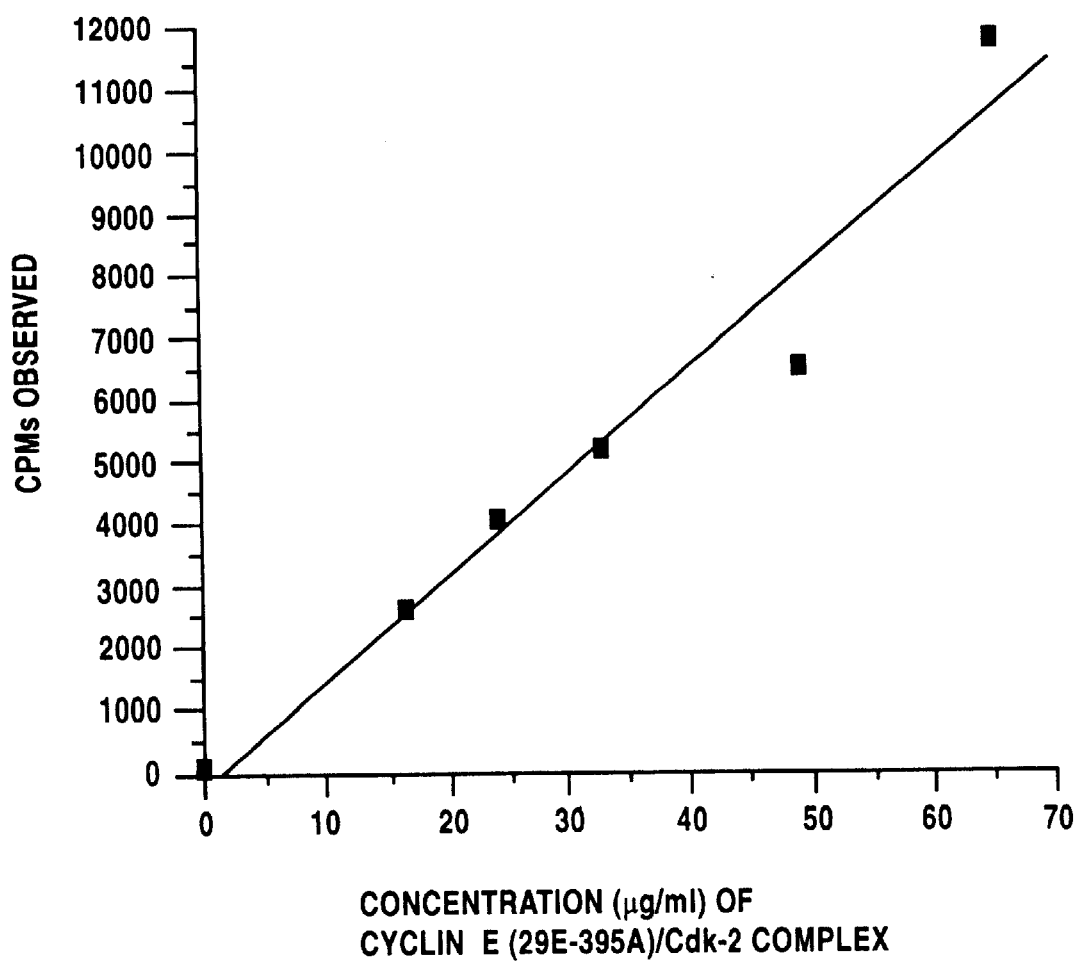

FIG. 14. Kinase activity of (MRHHHHHHK)-(29E-395A)-(SAWRHPQFGG)/cdk2 complex (SEQ. ID. NO. 7/cdk2 complex). The complex (2 μl) at a final concentration of 50 μg/ml is incubated for 30 min at 37° C. in 15 μl buffer containing 40 mM Tris/pH 7.5, 10 mM MgCl$_2$, 1 mM DTT, 0.1 mg/ml BSA, and 0.068 mg/ml histone and [$^{33}$P] ATP (approximately 1 μCi.). After 30 min at 37° C., 10 μl of the sample is spotted on a phosphocellulose paper, washed with 1% phosphoric acid for 10 min and repeated two more times. The paper is washed with acetone, dry heated for 5 min, and counted for radioactivity. The Y-axis is Cpm's observed. The X-axis shows the concentration (μg/ml) of the cyclinE(29E-395A)/Cdk-2 complex.

Figure 15:
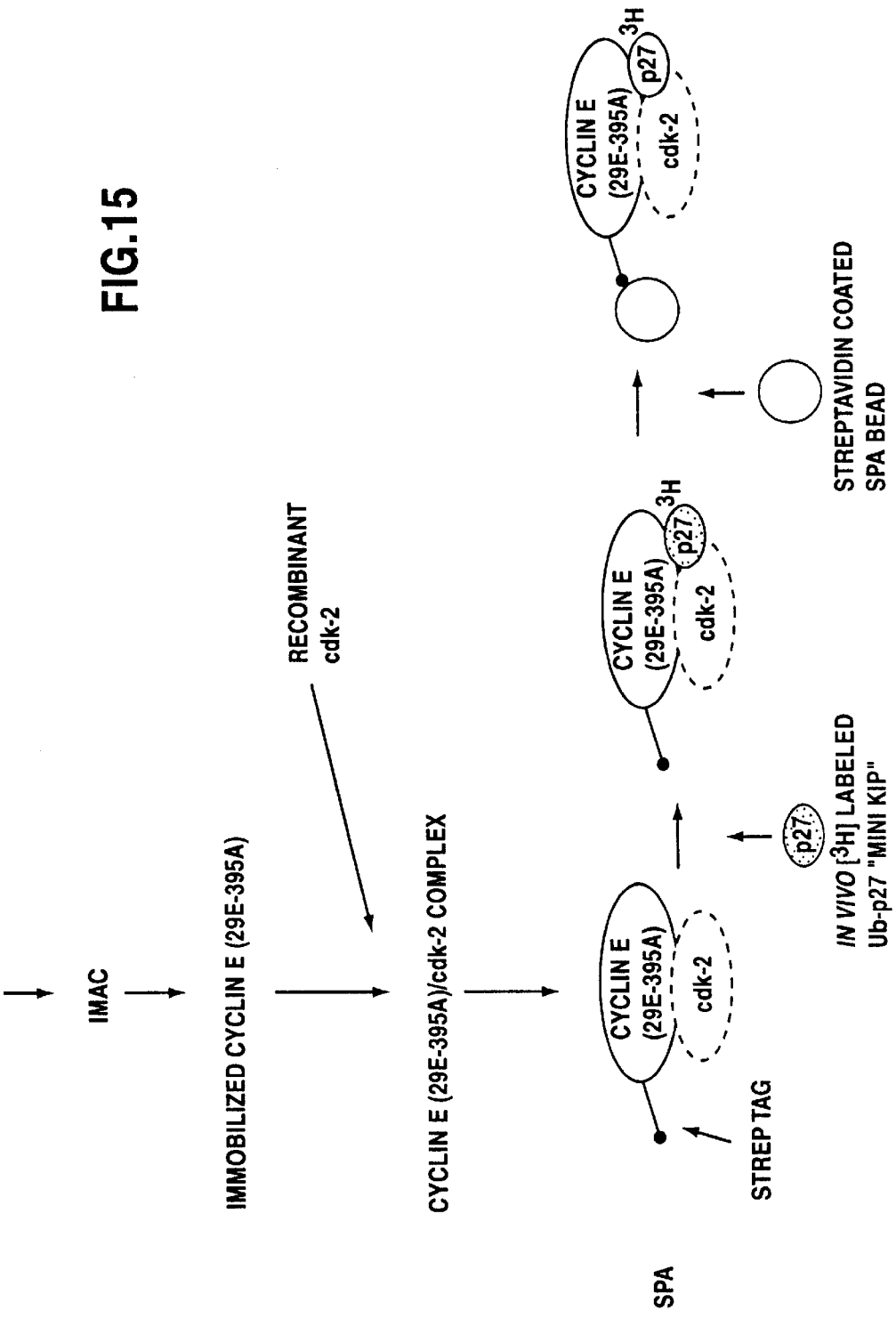

FIG. 15. Schematic for screening mimetics of the p27 kinase inhibitory protein (Kip) using scintillation proximity assay (SPA).

Figure 16:
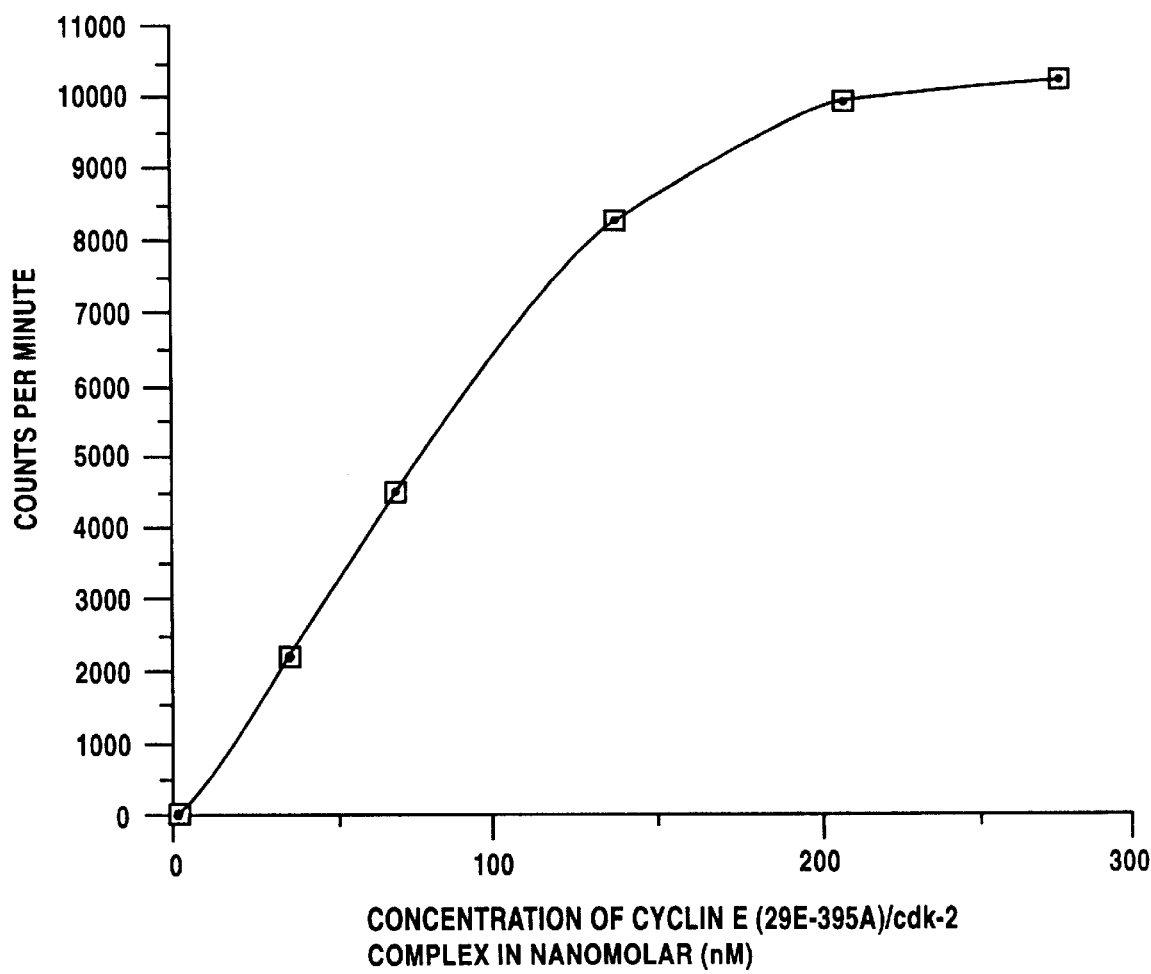

FIG. 16. Binding of [$^3$H] Ub-p27 minimal domain to (MRHHHHHHK)-(29E-395A)-(SAWRHPQFGG)/cdk2 complex (SEQ. ID. NO. 7/cdk2 complex) in SPA. SPA counts (Y-axis, CPM observed) as a function of (MRHHHHHHK)-(29E-395A)-(SAWRHPQFGG)/cdk2 complex (SEQ. ID. NO. 7/cdk2 complex) (X-axis, nM of complex) in the presence of 200 nM of [$^3$H] Kip. Streptavidin coated SPA beads were resuspended in assay buffer (30 mM HEPES, pH 7.5, 7.5 mM MgCl2, 1 mM DTT) to a 10× concentration of 20 mg/ml. Varying amounts of (MRHHHHHHK)-(29E-395A)-(SAWRHPQFGG)/cdk2 complex (SEQ. ID. NO. 7/cdk2 complex) and 0.58 μg of [$^3$H] labeled Ub-p27 minimal domain (such as the minimal domains disclosed in Polyak et al., Cell, (1994) 78:59–66, were addded in a total volume of 100 μl in fresh assay buffer. SPA beads (20 mg/ml) were diluted to 2 mg/ml in assay buffer and 100 μl was added to the samples. The assay was incubated on ice for 30 min. and the solution transferred to 3 ml scintillation vials and counted on a Packard Tricarb 1900. The SPA activity was expressed as counts per minute (CPM). The Y-axis is counts per minute (cpm). The X-axis is the concentration of cyclinE (29E-395A)/cdk-2 complex in nanomolar (nM).

SUMMARY OF THE INVENTION

This invention comprises various cyclin e constructs, complexes, the processes of making them, all the intermediates and the products produced from those processes.

PEST claims, PEST-DNA, such as, a nucleic acid polymer, designated cyclin E-PEST*-His6, coding for the polypeptide shown in FIG. 2, and related or redundant polymers coding for substantially the same polypeptide, the DNA sequence designated cyclin E-PEST*-His6, comprising the DNA sequence shown in FIG. 1, a biological composition, designated GST-Cyclin E-PEST*-His6, comprising the nucleic acid polymer of cyclin E-PEST*-His6, or FIG. 2, having its 5' end bound to nucleic acid coding for glutathione S-transferase (GST). A biological composition, designated His6-Cyclin E-PEST*-His6, comprising the nucleic acid polymer of yclin E-PEST*-His6, or FIG. 2 having its 5' end bound to nucleic acids coding for His6.

Amino acids transcribed from PEST DNA are disclosed. Such as, a polypeptide, designated cyclin E-PEST*-His6, comprising the amino acid sequence shown in FIG. 2, and equivalent substitutions thereof. A polypeptide comprising the amino acid sequence shown in FIG. 2, designated GST-Cyclin E-PEST*-His6, having its N-terminus bound to glutathione S-transferase (GST). A PEST polypeptide in close association with Cdk2. A polypeptide designated His6-Cyclin E-PEST*-His6, having its N-terminus bound to His6 and optionally formed in a complex or in close association with Cdk2.

A PEST-PCR oligonucleotide primer is disclosed, that being 5'-GCAGATCTTCAGTGGTGGTGGTGGTGGTGGCTC-TGCTTCTTACCG CCCTGTGCCGCGATGAGGAGCC-3'. (SEQ. ID. NO. 13)

PEST plasmids such as cyclin E-PEST*-His6 fusion plasmids. A fusion plasmid, designated cyclin E-PEST*-His6 fusion plasmid, that codes for cyclin E-PEST*-His6 polypeptide, that is made from a plasmid produced from a PCR reaction where there is a PCR oligonucleotide 3' primer and a 5' primer and the 3' primer is 5'-GCAGATCTTCAGTGGTGGTG GTGGTGGTG-GCTCTGCTTCTTACCG CCCTGTGCCGCGATGAGGAGCC-3' (SEQ. ID. NO. 13) and the 5' primer is an oligonucleotide having a cloning site and a site having nucleic acids identical to the 5' end of cyclin E and the PCR reaction amplifies native cyclin E. A fusion plasmid as above where the site having nucleic acids identical to the 5' end of cyclin E are the following nucleic acids, ATGAAGGAGGACGGCGGCG (SEQ. ID. NO. 19). A fusion plasmid as above where the 5' primer has a cloning site that is GATCAGATCTC (SEQ. ID. NO. 20). A fusion plasmid as above where the primer is an oligonucleotide having a cloning site and a site having nucleic acids identical to the 5' end of cyclin E, where the nucleic acids sequence is GATCAGATCTCATGAAGGAGGACGGCGGCG, (SEQ. ID. NO. 14) where the underlined nucleic acids are the cloning site and the nonunderlined nucleic acids are the nucleic acids identical to the 5' end of cyclin E.

Several GST/his6-cyclin E-PEST*-His6 fusion plasmids are described, such as a fusion plasmid, designated GST/his6-cyclin E-PEST*-His6 fusion plasmid, that codes for either glutathione S-transferase (GST)-cyclin E-PEST*-His6 polypeptide, or the His6-Cyclin E-PEST*-His6 polypeptide that is made from a plasmid produced from a PCR reaction where there is a PCR oligonucleotide 3' primer and a 5' primer and the 3' primer is 5'-GCAGATCTTCAGTGGTGGTGGTGGTGGTGGCTC-TGCTTCTTACCG CCCTGTGCCGCGATGAGGAGCC-3' (SEQ. ID. NO. 13) and the 5' primer is an oligonucleotide having a cloning site and a site having nucleic acids identical to the 5' end of cyclin E and the PCR reaction amplifies native cyclin E and this product is then subcloned into a fusion plasmid where the fusion plasmid contains either a GST or a His6 coding region at the 5' end, that codes for either the (GST)-cyclin E-PEST*-His6 polypeptide, or the His6-Cyclin E-PEST*-His6 polypeptide. A fusion plasmid where the fusion plasmid is derived from pRSET-A (Invitrogen) that codes for the His6-Cyclin E-PEST*-His6 polypeptide is described as well as a fusion plasmid where the fusion plasmid is derived from pGEX-2T(Pharmacia) that codes for the (GST)-cyclin E-PEST*-His6 polypeptide.

Recombinant PEST-bacteria are described, such as, bacteria that express either the glutathione S-transferase (GST)-cyclin E-PEST*-His6 fusion plasmid, or the His6-Cyclin E-PEST*-His6 fusion plasmid comprising, either the GST-cyclin E-PEST*-His6 polypeptide, or the His6-cyclin E-PEST*-His6 polypeptide. Bacteria where the bacteria contain GST-cyclin E fusion plasmids. Bacteria where the bacteria contain His6-cyclin E fusion plasmids. Bacteria where the bacteria is of the type E. coli.

Recombinant PEST-baculovirus, direct type, are described, such as a baculovirus, created by subcloning a linear GST/his6-cyclin E-PEST*-His6 nucleic acid fragment into a baculoviral transfer vector, and then co-transfecting this product into a baculovirus host cell with baculoviral DNA. Specific examples of this such as a baculovirus where the Baculoviral DNA is aculoGold crippled baculoviral DNA is described and also a few of the many suitable baculovirus transfer vectors and their use is described such as where the baculovirus transfer vector is pAcGHLT-C or pVL1392.

Recombinant PEST-baculovirus, made from products of PCT reactions are described, such as a baculovirus, created by subcloning a PCR product, created from a PCR reaction starting with DNA that codes for either His6-cyclin E-PEST*-His6, or GST-cyclin E-PEST*-His6, where the PCR product is subcloned into a baculoviral transfer vector, where the baculoviral transfer vector comprising the PCR product is co-transfected into a baculovirus host cell with baculoviral DNA. The baculovirus where the PCR product is from linear GST-cyclin E-PEST*-His6 nucleic acid. The baculovirus where the PCR product is linear His6-cyclin E-PEST*-His6 nucleic acid. Baculovirus baculovirus transfer vectors are pAcGHLT-C or pVL1392. Baculovirus where the baculovirus host cell DNA is BaculoGold crippled baculoviral DNA from PharMingen.

Cells expressing (GST)-cyclin E-PEST*-His6 polypeptide, or the His6-Cyclin E-PEST*-His6 polypeptide are also described, such as, cells containing a baculovirus that express either the glutathione S-transferase (GST)-cyclin E-PEST*-His6 polypeptide, or the His6-Cyclin E-PEST*-His6 polypeptide. Various cell types are described, including, prokaryotes, eukaryotes, cells that are derived from insect cells, cells are created from a PCR reaction beginning with linear (GST)-cyclin E-PEST*-His6 DNA, or His6-Cyclin E-PEST*-His6 DNA, cells where the PCR reaction begins with linear (GST)-cyclin E-PEST*-His6 DNA, cells of the insect type cells known as Sf 9 or High Five type cells, cells derived from mammals and cells derived from yeast.

Various complexes or close associations of two or more types of proteins or molecules are also described, such as, the protein complex comprising glutathione S-transferase (GST)-cyclin E-PEST*-His6 polypeptide, or the His6-Cyclin E-PEST*-His6 polypeptide with cdk2.

The methods of producing any of the cyclin E-PEST*-His6, GST-cyclin E-PEST*-His6, His6-cyclin E-PEST*-His6; DNA, amino acids, oligonucleotide primers, fusion plasmids, bacteria or baculovirus as described in any of the claims herein.are also described. The method of using glutathione affinity chromatography to produce purified glutathione S-transferase (GST)-cyclin E-PEST*-His6 polypeptide/cdk2 complexes, or His6-Cyclin E-PEST*-His6 polypeptide/cdk2 complex is also described.

Any of the cyclin E-PEST*-His6, GST-cyclin E-PEST*-His6, His6-cyclin E-PEST*-His6; DNA, amino acids, oligonucleotide primers, fusion plasmids, bacteria or baculovirus as products themselves are described as being produced or created from the methods and processes described herein.

In addition to the PEST constructs this application discloses various constructs that are sometimes herein referred to as the MSG constructs. The MSG constructs are also labeled or named after unique amino acids and reference to previously published sequences of amino acids related to the cyclin E protein. Thus, "MSG" may be (MRHHHHHHK)-(29E-395A)-(SAWRHPQFGG) (SEQ. ID. NO. 7) and the DNA that codes for it.

Described herein are nucleic acid polymers, coding for the polypeptide designated 29E-395A, shown in FIG. 9 or SEQ. ID. NO. 6, and related or redundant polymers coding for substantially the same polypeptide, where MSG is the DNA that codes for (MRHHHHHHK)-(29E-395A)-(SAWRHPQFGG) (SEQ. ID. NO. 7). A nucleic acid polymer comprising the DNA sequence shown in FIG. 8, or SEQ. ID. NO. 5, and equivalents thereof. The nucleic acids that code for the polypeptide, (MRHHHHHHK)-(29E-395A)-(SAWRHPQFGG), (SEQ. ID. NO. 7), attached to the nucleic acids that code for the N-terminal sequence (MRHHHHHHK) (SEQ. ID. NO. 9) and the C-terminal sequence (SAWRHPQFGG) (SEQ. ID. NO. 11). A nucleic acid polymer comprising the DNA sequence shown in Sequence Listing number 8, (SEQ. ID. NO. 8) and equivalents thereof.

Various MSG amino acids and complexes are described, such as, a polypeptide, designated 29E-395A, shown in FIG. 9 or Sequence Listing number 6, (SEQ. ID. NO. 6). A polypeptide with following amino acids attached to the N-terminal end, (MRHHHHHHK) (SEQ. ID. NO. 9) and the following amino acids attached to the C-terminal end, (SAWRHPQFGG), (SEQ. ID. NO. 11), thus providing the polypeptide designated, (MRHHHHHHK)-(29E-395A)-(SAWRHPQFGG), (SEQ. ID. NO. 7). Any of these MSG polypeptides in close association with Cdk2 or GroEL.

The MSG/GroEL complex, by itself, and produced from a process is described. A complex of MSG with GroEL, when the complex is purified after the expression of MSG from bacterial cells, when NaCl is present during cell lysis and purification. The complex where the complex is purified using either immobilized metal affinity chromatography (IMAC) or immobilized streptavidin. The complex where the complex is purified using immobilized metal affinity chromatography (IMAC). Any of these GroEL complexs where the NaCl concentration is about 0.5 M.

The MSG/cdk 2 complex, by itself, and produced from a process is described. A complex of MSG with cdk2, when the complex is produced from the expression of MSG from bacterial cells, when cdk2 is present during subsequent purification. The complex where the complex is purified using either immobilized metal affinity chromatography (IMAC) or immobilized streptavidin. The complex where the MSG is first immobilized on a column and the complex then created by exposing the immobilized MSG to cdk2. The complex where the cdk2 is recombinant cdk2 expressed from baculovirus infected insect cells.

The process of making the MSG/GroEL complex is described. The process of preparing a complex of MSG with GroEL, by expressing MSG from bacterial cells, followed by purification of the MSG, with NaCl present during cell lysis and purification. The complex where the complex is purified using either immobilized metal affinity chromatography (IMAC) or immobilized streptavidin. The process where the NaCl concentration is about 0.5 M is described.

The complex itself and the process of making the MSG/cdk2 complex is described. The process of preparing a complex of MSG with cdk2, by expressing and puriying the MSG from bacterial cells, and having cdk2 present during the purification. The process where the MSG expressed from bacterial cells is first immobilized on a column and the complex of MSG with cdk2 is created by exposing the immobilized MSG to cdk2. The complex and process where the complex is purified using either immobilized metal affinity chromatography (IMAC) or immobilized streptavidin and where the cdk2 is recombinant cdk2 expressed from baculovirus infected insect cells is described.

In addition, MSG; DNA, amino acids, oligonucleotide primers, fusion plasmids, bacteria or baculovirus related to MSG are described herein as being produced or created from the methods and processes described herein.

ADDITIONAL DETAILS AND DESCRIPTION OF THE INVENTION

Definitions.

In this document, names, acronyms, descriptions etc. may be in either UPPER or lower case with no distinction in meaning. Alternatively UPPER and lower case letters may be used interchangably for any reason, unless indicated otherwise.

His6 refers to 6 sequential histidine amino acids, or the nucleic acids that code for these molecules.

M.o.i. is multiplicity of infection.

The term "native conditions" refers to proteins not denatured.

PCR primers or oligonucleotides described herein may be constructed one skilled in the art or they may even be custom ordered from vendors. For example, most of the primers used herein are first designed by the inventors then ordered and purchased from Genosys, Tex. Genosys Biotechnologies Inc., 1442 Lakefront Circle, Suite 185, The Woodlands, Tex. 77380.

Specific embodiments or descriptions of general items, procedures or descriptions should be consdered to illuminate and not limit the invention in any way.

General Description.

The PEST motif is a stretch of amino acids having a specific composition, and its presence in some proteins is known to cause the rapid degradation of eukaryotic cells. The mutation of these motifs in a cyclin might therefore result in the abnormal persistance of high levels of cyclin, and this may contribute to tumorigenesis.

The human cyclin E protein contains a region (amino acids 369–385) that resembles the PEST motif. Demonstration that this region is a bona fide PEST motif would be valuable in dissecting the function of cyclin E. A complex lacking the PEST motif would simulate potentially tumorigenic mutations. Furthermore, such a cyclin E complex might also produce higher levels of recombinant cyclin E protein in eukaryotic cells, thus facilitating production and purification.

Comparison of p21 and p27 suggest a highly conserved N-terminal region that retains cdk inhibitory activity. Specifically, p21 cdk inhibitory activity appears in a region that corresponds to amino acids 22 to 71. Likewise, amino acids 28 to 79 of p27 are sufficient to inhibit Cdk activity in vitro. The inhibitory activity of these small polypeptides supports the notion that inhibitory activity of these KIPs might be mimicked by small organic molecules.

Recent studies suggest that increased expression of cyclin E and Cdk2 may be important in the oncogenic transformation of HUT 12 cells. Increased expression of the p21 and p27 cell cycle inhibitors resulted in inhibition of cyclin E/cdk2 activity, resulting in cell cycle arrest. These results support the hypothesis that Cdk2/cyclin E is a rate-limiting target of the complex regulatory pathway during eukaryotic cell cycle. Taken together, these results suggest that cdk2/cyclin E may be an important therapeutic target.

The present invention relates to novel special constructs and complexes of human cyclin E with cdk2. According to the present invention, active protein kinase complexes including GST-cyclin E-PEST*-His6 and cdk2 can be produced by either mixing components that have been purified separately, or by co-purifying from cells that co-express the genes for GST-cyclin E-PEST*-His6 and cdk2. These complexes are said to be in close association with each other. The close association complexes have special enzymatic properties. In another embodiment, active protein kinase complexes may also be produced using E. coli derived human cyclin E (MRHHHHHHK-29E-395A-SAWRHPQFGG) (SEQ. ID. NO. 7). Cyclin E (MRHHHHHHK-29E-395A-SAWRHPQFGG) (SEQ. ID. NO. 7) is immobilized to an affinity matrix and is eluted as a soluble complex in the presence of cdk2. Alternatively, a special complex of human cyclin E (MRHHHHHHK-29E-395A-SAWRHPQFGG) (SEQ. ID. NO. 7) may be coexpressed with cdk2 in baculovirus infected insect cells and purified from crude extract as a complex.

The special constructs of cyclin E/cdk2 complexes described herein are active kinases and can be used in screening for inhibitors of kinase activity. The present invention also relates to a method of detecting mimetics of the p21/p27 family of cyclin-dependent kinase inhibitors (also known as the KIPs). According to another embodiment of the present invention, biotinylated special complex cyclin E/cdk2 complexes are adsorbed to streptavidin-coated SPA beads, and a radiolabeled KIP species is added. Alternatively, the special cyclin E (MRHHHHHHK-29E-395A-SAWRHPQFGG)/cdk2 (SEQ. ID. NO. 7/cdk2) is adsorbed to streptavidin-coated SPA beads by virtue of the presence of a strep tag at the C-terminus of cyclin E of the special construct. When a radiolabeled KIP, such as p27, binds to cyclin E/cdk2 special complex on the SPA beads, it produces scintillation registered as counts/min or CPM. In the presence of a small molecular weight KIP mimetic, an inhibition in scintillation signal would result in a decrease in CPM.

The present invention comprises novel special constructs and complexes of human cyclin E and methods for obtaining these special cyclin E/cdk2 complexes. Specifically, the invention includes the production of complexes between GST-cyclin E-PEST*-His6 and cdk2; the identification of complexes between E. coli expressed human cyclin E (MRHHHHHK)-(29E-395A)-(SAWRHPQFGG) (SEQ. ID. NO. 7) and the bacterial chaperonin GroEL; and E. coli expressed special complex of human cyclin E (MRHHHHHK)-(29E-395A)-(SAWRHPQFGG) (SEQ. ID. NO. 7) and recombinant cdk2 from baculovirus infected insect cells. The present invention also provides a method for obtaining soluble, active complexes of special complex cyclin E with Cdk2 for identifying inhibitors of kinase activity of the complex.

The present invention relates to the construction of special complexes of human cyclin E. This disclosure describes two unique forms of recombinant human cyclin E. The first of these, herein referred to as GST-cyclin E-PEST*-His6, contains amino acid differences at four positions compared to the wild type gene, resulting in the destruction of the putative "PEST" degradation targeting motif (FIG. 4). It also includes a glutathione S-transferase (GST) tag on the N-terminus to facilitate purification by glutathione affinity chromatography and a hexahistidine (His6) tag on the C-terminus of the polypeptide to facilitate purification by immobilized metal affinity chromatography (IMAC).

The second cyclin E construct, herein referred to as cyclin E (MRHHHHHHK)-(29E-395A)-(SAWRHPQFGG), (SEQ. ID. NO. 7) contains a truncated version of recombinant human cyclin E that contains the amino acid sequence from 29E to 395A and is capable of being recognized by cdk2. The cyclin E construct (29E-395A) is equipped with an N-terminal histidine tag (MRHHHHHHK) (SEQ. ID. NO. 9) to facilitate purification by immobilized metal affinity chromatography (IMAC) and a 10 amino acid C-terminal tag (SAWRHPQFGG) (SEQ. ID. NO. 11) with binding affinity for streptavidin.

The present invention relates to methods for generating large amounts of soluble, active complex of GST-cyclin E-PEST*-His6/cdk2 or cyclin E (MRHHHHHHK)-(29E-395A)-(SAWRHPQFGG)/cdk2 (SEQ. ID. NO. 7/cdk2) useful for research and in vitro screening inhibitors of its kinase activity. The present invention also relates to a method for generating complexes of GST-cyclin E-PEST*-His6/cdk2 or cyclin E (MRHHHHHHK)-(29E-395A)-(SAWRHPQFGG)/ cdk2 (SEQ. ID. NO. 7/cdk2) with a radiolabeled minimal domain of the kinase inhibitory protein (KIP) p27, and usefulness of this assay system for screening KIP mimetics.

Transient protein-protein interactions are known to control a number of fundamental cellular processes such as cell cycle, cell growth, metabolic pathways, and signal transduction. It is relatively difficult to set up in vitro high volume screens for inhibitors that would interrupt such protein-protein interactions. For streptavidin-coated scintillation proximity assays (SPAs), one of the protein partners is usually biotinylated in vitro. The cdk2/human cyclin E (MRHHHHHHK)-(29E-395A)-(SAWRHPQFGG) (SEQ. ID. NO. 7/cdk2) complex of the present invention can be directly recognized by immobilized streptavidin by virtue of the presence of a 10 amino acid C-terminal tag. Alternatively, either the cdk2/human cyclin E (MRHHHHHHK)-(29E-395A)-(SAWRHPQFGG) (SEQ. ID. NO. 7) complex or the cdk2/GST-cyclin E-PEST*-His6 complex can be biotinylated and then bound by streptavidin. These complexes can be adsorbed to streptavidin coated SPA beads, and in the presence of a radiolabeled Kip, an increase in scintillation is observed due to specific interaction of the KIP with the complex. A disruption of interaction by inhibitors should result in a decrease in SPA counts. The present invention also relates to utility of such assays in identifying KIP mimetics.

The special complex cyclin E-PEST*-His6/cdk2 was constructed by mutation of four amino acids in the C-terminus of cyclin E. These amino acids occur within a region (amino acids 369–385) that fits the pattern of the PEST motif. PEST motifs are known to be responsible for the targeted proteolytic degradation of other proteins, and had been predicted to provide this function as part of cyclin E.

The GST-cyclin E-PEST*-His6 construct described herein may also be attached to GST and His6 affinity tags to simplify purification and detection. The protein can be produced in an expression system, for example using the baculovirus insect cell system, and can be purified by either glutathione affinity chromatography (for GST) or immobilized metal affinity chromatography (IMAC).

The special complex cyclin E gene coding for a truncated (29E-395A) form of the protein was cloned and produced in E. coli as a fusion protein. The cyclin E construct (29E-395A) is equipped with an N-terminal histidine tag (MRHHHHHHK) (SEQ. ID. NO. 9) to facilitate purification by immobilized metal affinity chromatography (IMAC) and a 10 amino acid C-terminal tag (SAWRHPQFGG) (SEQ. ID. NO. 11) with binding affinity for streptavidin.

Under defined conditions, the fusion protein (MRHHHHHHK)-( 29E-395A)-(SAWRHPQFGG) (SEQ. ID. NO. 7) isolated from crude E. coli lysates is copurified with an unexpected ~60 KD protein. This latter protein is identified as GroEL, the bacterial equivalent of the mammalian 60 KD heat shock protein (hsp60). The cyclin E preparation thus obtained is soluble and is active in a kinase assay in the presence of recombinant cdk2 purified from baculovirus infected insect cells. The fusion protein (MRHHHHHHK)-(29E-395A)-(SAWRHPQFGG) (SEQ. ID. NO. 7) isolated without GroEL is insoluble.

Recombinant cdk2 can substitute for GroEL and, can be used to produce soluble, active cdk2-human cyclin E (MRHHHHHHK)-(29E-395A)-(SAWRHPQFGG) (SEQ. ID. NO. 7) complex. Thus, recombinant cdk2, produced by baculovirus-infected insect cells, is allowed to interact specifically with matrix-bound recombinant human cyclin E. This matrix-bound complex can be eluted in a soluble form, has kinase activity and binds to a radiolabeled minimal domain of the kinase inhibitory protein (KIP) p27. See Polyak et al., Cell, (1994) 78:59–66, for minimal domains of p27. Matrix-bound human cyclin E (MRHHHHHHK)-(29E-395A)-(SAWRHPQFGG) (SEQ. ID. NO. 7) eluted without recombinant cdk2, is insoluble.

Without intending to be inclusive, the invention described herein includes the following characteristics.

The GST-cyclin E-PEST*-His6 protein encoded by the genetic construct described herein is capable of binding to and activating cdk2.

The GST-cyclin E-PEST*-His6 protein has a longer half-life in mammalian cells than does full-length, wild type cyclin E protein.

There is an association between human cyclin E (MRHHHHHHK)-(29E-395A)-(SAWRHPQFGG) (SEQ. ID. NO. 7) and GroEL from E. coli cells.

Suprising, unexpected, dramatic production of a soluble human cyclin E (MRHHHHHHK)-(29E-395A)-(SAWRHPQFGG) (SEQ. ID. NO. 7) associated with GroEL became possible by the fortuitous use of 0.5 M NaCl, under native conditions, during E. coli cell lysis, followed by isolation by immobilized metal affinity chromatography (IMAC).

The GroEL-associated complex of human cyclin E (MRHHHHHHK)-(29E-395A)-(SAWRHPQFGG) (SEQ. ID. NO. 7) is active in binding to cdk2, resulting in kinase activity.

Recombinant cdk2, produced by baculovirus-infected insect cells, binds specifically to matrix-bound recombinant human cyclin E (MRHHHHHHK)-(29E-395A)-(SAWRHPQFGG), (SEQ. ID. NO. 7) resulting in elution of a soluble complex of cyclin E (MRHHHHHHK)-(29E-395A)-(SAWRHPQFGG) (SEQ. ID. NO. 7) and cdk2.

The cdk2-human cyclin E (MRHHHHHHK)-(29E-395A)-(SAWRHPQFGG) (SEQ. ID. NO. 7) complex is active in a kinase activity assay.

The cdk2-human cyclin E (MRHHHHHHK)-(29E-395A)-(SAWRHPQFGG) (SEQ. ID. NO. 7) complex can be directly recognized by immobilized streptavidin by virtue of the presence of a 10 amino acid C-terminal tag.

Presence of a genetically engineered C-terminal tag, with affinity for streptavidin, obviates the need to biotinylate cdk2-cyclin E complex.

DETAILED DESCRIPTION OF THE CONSTRUCTION, MANIPULATION AND USES OF THE SPECIAL CONSTRUCTS

The present invention relates to novel special versions of human cyclin E. According to the present invention, the desired special versionsof human cyclin E are produced by recombinant DNA technology and are purified as fusion proteins. The fusion proteins are produced by host cells into which the genetic information encoding the fusion proteins has been introduced. The host cells may secrete the fusion protein into the culture media or store it in the cells whereby the cells must be disrupted in order to extract the product. As hosts, any eukaryotic cells, including both *E. coli*, and baculovirus infected insect cells and yeast are possible hosts.

For purification using the His6 tag, the cell extract containing the fusion protein is passed through a column containing immobilized $Ni^{2+}$. The immobilized metal ion chelates the protein. This impedes the movement of the protein through the column. Both the GST-cyclin E-PEST*-His6 and the cyclin E construct (29E-395A) are equipped with a terminal His6 tag to facilitate purification by immobilized metal affinity chromatography (IMAC).

For purification or immobilization of the GST-cyclin E-PEST*-His6 protein using the GST tag, cell extract is passed over a glutathione affinity column. In addition, the cyclin E (MRHHHHHHK)-(29E-395A)-(SAWRHPQFGG) (SEQ. ID. NO. 7) special version includes a 10 amino acid C-terminal tag (SAWRHPQFGG) (SEQ. ID. NO. 11) with binding affinity for streptavidin.

Under defined conditions, human recombinant human cyclin E (MRHHHHHHK)-(29E-395A)-(SAWRHPQFGG) (SEQ. ID. NO. 7) isolated from crude *E. coli* lysates is copurified with an unexpected ~60 KD protein identified as GroEL, the bacterial equivalent of the mammalian 60 KD heat shock protein (hsp60). The cyclin E preparation thus obtained is soluble and is active in a kinase assay in the presence of recombinant cdk2 from baculovirus infected insect cells. Human recombinant special cyclin E (MRHHHHHHK)-(29E-395A)-(SAWRHPQFGG) (SEQ. ID. NO. 7), isolated without GroEL, is insoluble.

In another embodiment of the present invention, recombinant cdk2 can substitute for GroEL, and can be used to produce soluble active cdk2-recombinant human cyclin E (MRHHHHHHK)-(29E-395A)-(SAWRHPQFGG) (SEQ. ID. NO. 7) complex. Employing this embodiment, recombinant cdk2, produced by baculovirus-infected insect cells, is allowed to interact specifically with matrix-bound recombinant human cyclin E (MRHHHHHHK)-(29E-395A)-(SAWRHPQFGG) (SEQ. ID. NO. 7). This matrix-bound complex can be eluted in a soluble form, and has kinase activity which can be stimulated in the presence of a cyclin-dependent activating kinase (CAK). Matrix-bound human recombinant cyclin E (MRHHHHHHK)-(29E-395A)-(SAWRHPQFGG) (SEQ. ID. NO. 7), eluted without recombinant cdk2, is insoluble.

Native conditions that favor dissociation of GroEL, i.e., absence of 0.5M NaCl during cell lysis and IMAC purification, produces insoluble fusion protein containing truncated cyclin E. Therefore, the fortuitous use of 0.5 M NaCl, under native conditions, during cell lysis and isolation by immobilized metal affinity chromatography (IMAC) results in the surprising and unexpected increased production, relative to conditions without NaCl, of a fusion protein containing soluble human cyclin E (MRHHHHHHK)-(29E-395A)-(SAWRHPQFGG) (SEQ. ID. NO. 7) associated with GroEL. The N-terminal tag (MRHHHHHHK) (SEQ. ID. NO. 9) allows immobilization of the fusion protein. This step is essential for copurification with GroEL which in turn allows recovery of a soluble complex useful for studying kinase activity in the presence of added cdk2. Likewise, cdk2 protein can be used to interact with immobilized cyclin E and this allows recovery of a soluble complex which is active as a kinase.

In another embodiment of this invention, the C-terminal strep tag, SAWRHPQFGG, is used to facilitate immobilization of the complexes to streptavidin coated SPA beads. This eliminates the need to chemically modify the fusion protein by biotinylation prior to its use in SPA-based screening assays.

According to the present invention, under native conditions, cyclin E special construct, (MRHHHHHHK)-(29E-395A)-(SAWRHPQFGG), (SEQ. ID. NO. 7) expressed in *E. coli*, requires a partner protein for solubilization. We have identified these two sources as Gro EL from the *E. coli* host and purified recombinant cdk2 from baculovirus infected insect cells.

The present invention provides a functional complex of cdk2/GST-cyclin E-PEST*-His6 and cdk2/cyclin E (MRHHHHHHK)-(29E-395A)-(SAWRHPQFGG) (SEQ. ID. NO. 7) which are suitable for anti-cdk2/cyclin E screening purposes. The method of our invention yields active complexes which contain both the regulatory (special cyclin E) and catalytic subunit (cdk2) subunits.

Description of the Special GST-cyclin E-PEST*-His6 Construct.

FIGS. 1 and 2 show the DNA and amino acid sequences for GST-cyclin E-PEST*-His6, respectively. FIG. 3 shows a comparison of the GST-cyclin E-PEST*-His6 to wild type cyclin E at the C-terminus (including the putative PEST region). A schematic diagram (A) of this construct is shown in FIG. 17.

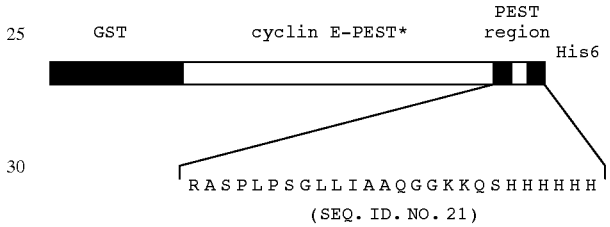

Scheme A

The following oligonucleotide, RH113, was used as a 3' primer for PCR mutagenesis of the cyclin E gene:

5'-GCAGATCTTCAGTGGTGGTGGTGGTGGTGGCTC-TGCTTCTTACCG
CCCTGTGCCGCGATGAGGAGCC-3' (SEQ. ID. NO. 13)

This primer makes the following point changes in the DNA sequence of human cyclin E: C1139→T, C1141→G, C1144→G, and A1150→G. (This numbering is according to FIG. 2 in Koff, et. al., *cell* 66:1217–1228. It also mutates all nucleotides 3' to C1224. These changes result in the following mutations in the amino acid sequence: T380→I, P381→A, P382→A, S384→G, and the replacement of the most C-terminal six amino acids (390–395) with six histidines. The primer also includes a BglII site to facilitate subcloning.

Once the above 3' PCR primer is selected, any suitable 5' primer may be used. The 5' primer should have a cloning site, i.e. cutting or ligating site and it should have a portion of the same sequence as cyclin E. The following oligonucleotide, KW133, was used as a 5' primer for PCR mutagenesis of the cyclin E gene:

5'-GATCAGATCTCATGAAGGAGGACGGCGGCG (SEQ. ID. NO. 14)

This primer changes the noncoding DNA sequence just 5' to the codon of the cyclin E gene to a BglII site, to facilitate subcloning. The underlined portion of the primer shows the cloning site, the non-underlined protion is identical to the 5' end of cyclin E.

These oligonucleotides are then used in PCR reactions, the resulting PCR products, or special cyclin E PCR products, may then be sub-cloned into any fusion plasmid, such as, pRSET-A (Invitrogen®) or pGEX-2T (Pharmacia®) for subsequent bacterial expression (direct expression) or they may be used as templates for amplification and subcloning into baculovirus vectors.

When the PCR primers are used for amplification and subcloning of GST-cyclin E-PEST*-His6 into suitable baculovirus transfer vectors, such as, pAcGHLT-C (PharMingen®) or pVL1392 they should incorporate restriction sites and additional nucleotides to maintain the open reading frame with the GST fusion protein of the vector. Provided the open reading frame with the GST fusion protein is maintained any suitable set of PCR primers should be acceptable for amplification and subcloning.

Recombinant baculoviruses are generated by co-transfection of baculovirus host cells, commonly insect cells. One of several suitable lines of cells is *Spodoptera frugiperda* (Sf) and one line of Sf cells used here was Sf 9. Sf cells with the transfer plasmid constructs described above were used with BaculoGold crippled baculoviral DNA (PharMingen) according to the manufacturer's instructions. Any suitable baculovirus could be used in place of BaculoGold. Resultant viruses are purified by propagating single plaques from three consecutive plaque purification assays.

In addition to the GST-cyclin E-PEST*-His6 construct expression, cdk2 must also be expressed in order to create a special complex of GST-cyclin E-PEST*-His6/cdk2. Baculovirus which express cdk2 may be cloned and propagated according to literature references and should be known to one skilled in the art. Sf 9 and baculovirus propagation may follow the procedures of Summers and Smith.

Co-expression of the GST-cyclin E-PEST*-His6 and the cdk2-HA baculoviruses may be performed in either Sf 9 or High Five cells (BTI-TN-5B1-4, derived from Trichoplusia ni). Sf 9 cells are grown in spinner culture at 28° C. to $10^6$ cells/ml in Grace's medium (GIBCO/BRL) supplemented with 10% fetal bovine serum, 100 Units/ml penicillin G sodium and 100 ug/ml streptomycin sulfate. High Five cells are grown to $10^6$ cells/ml in shake flasks at 150 rpm containing InsectExpress medium (BioWhittaker). Cells are co-infected with special cyclin E baculoviruses at an m.o.i. of 20 and cdk2 baculovirus at an m.o.i. of 10. Cells are harvested by centrifugation at 48–68 hours post infection.

Purification of GST-cyclin E-PEST*-His6/cdk2 Complexes by Glutathione Affinity Chromatography Cell pellets are washed with phosphate buffered saline (PBS) and resuspended in hypotonic lysis buffer (10 mM Hepes, pH7.4/10 mM NaCl/1 mM EDTA/0.2 ug/ml leupeptin/0.2 ug/ml pepstatin/0.2 ug/ml aprotinin/0.2 mM AEBSF) at 1 ml for every $10^7$ cells initially infected. Cells are lysed on ice for 1 hour, then NaCl is added to a final concentration of 150 mM. Additionally, cells are sonicated on ice for 2 minutes. Lysates are clarified by high speed centrifugation. Ten volumes of lysate is mixed with 1 packed volume (pv) of washed glutathione Sepharose 4B (Pharmacia Biotech®) for 1 hour at 4° C. The Sepharose is pelleted by centrifugation at 1500 rpm, 8 minutes and washed by addition of 10 pv PBS plus 0.2% Nonidet P-40 and rocked for 10 minutes.

The Sepharose is pelleted at 1500 rpm for 8 minutes and washes repeated 2 additional times. After the final wash, the Sepharose is resuspended in PBS without detergent, loaded into a chromatography column, and the PBS drained. To elute bound material, 3 ml Elution Buffer (15 mM reduced glutathione in 50 mM Tris-HCl, pH8) per ml of pv of glutathione Sepharose 4B is added to the column and 1 ml fractions are collected. Aliquots of each fraction are analyzed by SDS-PAGE and Commassie or silver staining.

Additionally, samples are subjected to SDS-PAGE and Western analysis using anti-cyclin E, or anti-cdk2 antibodies (Upstate Biotechnology, Inc.). Fractions containing immunoreactive cyclin/cdk2-HA complexes are pooled. Stabilization buffer (10×: 50% glycerol/10 mM DTT/5 mM AEBSF/50 mM NaF/5 mM EGTA) is added to a final concentration of 1× to the pooled material and 1 ml aliquots are frozen on dry ice and stored at −80° C.

Description of the Special Cyclin E (MRHHHHHHK)-(29E-395A)-(SAWRHPQFGG) (SEQ. ID. NO. 7) construct. Also Known As (aka) the MSG construct.

This document may use the letters MSG in either upper or lower case letters as an abbreviated method of writing or refering to the special cyclin E (MRHHHHHHK)-(29E-395A)-(SAWRHPQFGG) (SEQ. ID. NO. 7) construct.

FIGS. 8 and 9 show the DNA sequence and amino acid sequence of special cyclin E expressed in *E. coli*, respectively. A complete schematic representation of this construct in terms of amino acid sequence is shown below. This shematic representation (B) is a short form of what is provided in full as SEQ. ID. NO. 7.

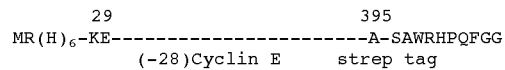

The 5' primer contained the sequence encoding for an EcoR1 restriction site as well as the region coding for the 5' end of human cyclin E starting with Glu(29).

```
                                                29 30
            MET ARG HIS HIS HIS HIS HIS HIS LYS GLU GLU MET    (SEQ. ID. NO. 15)

5' GGAA TTC CAT ATG CGA CAC CAT CAC CAT CAC CAT AAG GAA GAA ATG    (SEQ. ID. NO. 16)

ALA LYS ILE ASP ARG THR

GCC AAA ATC GAC AGG ACG 3'
```

The 3' primer contained the anti-sense sequence coding for a HindIII site at the 3' end of the human cyclin E and a streptavidin tag.

```
Hind III      GLY GLY PHE GLN PRO HIS ARG TRP ALA SER ALA    (SEQ.ID.NO.17)

5' CCC AAG CTT CTA TCC TCC AAA CTG GGG GTG TCT CCA TGC GCT CGC  (SEQ.ID.NO.18)

stop --------------------Strep tag-----------
    MET GLU PRO GLY SER SER GLN LYS

CAT TTC CGG CCC GCT GCT CTG CTT 3'
```

The desired DNA fragment is obtained by PCR from the human cyclin E gene and is restricted with EcoR1 and HindIII. This fragment is then inserted into Eco R1/HindIII cut pKK223-3 and transformed into *E. coli* strain JM-109. Colonies are selected for ampicillin resistance and analyzed by restriction enzyme digestion and expression. The clone S-18,1 was selected for expression of the special human cyclin E (MRHHHHHHK)-(29E-395A)-(SAWRHPQFGG) (SEQ. ID. NO. 7). Sequencing of the plasmid DNA was used to verify the construct.

Studies with *E. coli* expressed special human cyclin E (MRHHHHHHK)-(29E-395A)-(SAWRHPQFGG), (SEQ. ID. NO. 7) purified by IMAC in the presence of 0.5 M NaCl, show that GroEL (*E. coli* 60 kDa chaperonin) copurifies with this truncated version of human cyclin E (FIG. 10). The fortuitous use of 0.5 M NaCl, under native conditions, during cell lysis and isolation by immobilized metal affinity chromatography (IMAC) results in the unexpected production of a fusion protein containing soluble human cyclin E (29E-395A) associated with GroEL.

These protein protein complexes may be said to be associations where one protein is in "close association" with another protein. Frequently individual proteins will have no catalytic effects without being in close association with other proteins. This was earlier described in this document with reference to the GST-cyclin E-PEST*-His/cdk2 complex, where it is the complex or the close association of the two proteins that gives the association catalytic activity. Similarly here, with the (MRHHHHHHK)-(29E-395A)-(SAWRHPQFGG) (SEQ. ID. NO. 7) polymer, it is when the (MRHHHHHHK)-(29E-395A)-(SAWRHPQFGG) (SEQ. ID. NO. 7) polymer is in close association with GroEL or with cdk2 that this association has its special characteristics, in this latter case the special characteristic is good activity coupled with solubility. In this document, in association or in close association may be considered synonymous with complex.

The interaction of GroEL with Cyclin E is abolished when IMAC purification of special human cyclin E (MRHHHHHHK)-(29E-395A)-(SAWRHPQFGG) (SEQ. ID. NO. 7) is carried out in the absence of NaCl (FIG. 11). However, native conditions that favor dissociation of GroEL, ie: absence of 0.5M NaCl during cell lysis and IMAC purification, produces insoluble protein containing special cyclin E without GroEL. These results led us to conclude that a solubilizing partner is preferred and in this regard GroEL is important in the solubilization of special complex cyclin E proteins produced in *E. coli*.

Immobilization of Special Complex Cyclin E (MRHHHHHHK)-(29E-395A)-(SAWRHPQFGG) (aka MSG) or (SEQ. ID. NO. 7) and isolation of soluble MSG/GroEL complex and soluble MSG/Cdk2 complex Herein is described the use of cdk2 to substitute for Gro EL in solubilizing special cyclin E (MRHHHHHHK)-(29E-395A)-(SAWRHPQFGG) (SEQ. ID. NO. 7).

The N-terminal tag (MRHHHHHHK) (SEQ. ID. NO. 9) allows immobilization of the protein on immobilized nickel by virtue of the presence of neighboring histidines. This step is essential for copurification with GroEL which inturn allows recovery of a soluble complex useful for studying kinase activity in the presence of cdk2. The interaction of GroEL with cyclin E can be prevented by the absence of 0.5 M NaCl and this allows immobilization of special cyclin E special complex without GroEL.

When purified recombinant cdk2 from baculovirus infected insect cells is passed through a column containing immobilized special human cyclin E (MRHHHHHHK)-(29E-395A)-(SAWRHPQFGG) (SEQ. ID. NO. 7) produced in *E. coli*, a complex is formed on the column. This complex is eluted by using imidazole and the resulting cyclin E/cdk 2 complex is soluble (FIG. 12). Special cyclin E eluted in the absence of cdk2, under similar conditions, is insoluble. Therefore, cdk2 protein can also be used to interact with immobilized cyclin E and this allows recovery of a soluble complex which is active as a kinase.

Binding of cdk2/Human Cyclin E (MRHHHHHHK-29E-395A-SAWRHPQFGG) (SEQ. ID. NO. 7) complex to streptavidin FIG. 13 shows purification of the complex by affinity chromatography on immobilized streptavidin. As shown, the complex binds to the column and can be purified. The purified complex can be used for screening inhibitors of its kinase activity. In another embodiment, the complex can be used in assays requiring binding to streptavidin, for example, in a Scintillation Proximity Assay (SPA) based on streptavidin-coated beads.

Kinase Activity of Special Cyclin E-cdk2 Complexes.

Interestingly, neither GST-cyclin E-PEST*-His6/cdk2 complexes nor cyclin E (MRHHHHHHK)-(29E-395A)-(SAWRHPQFGG) (SEQ. ID. NO. 7)/cdk2 complexes require addition of a cyclin-dependent activating kinase (CAK) for kinase activity (FIGS. 5 and 14). These results show that both the GST-cyclin E-PEST*-His6/cdk2 and cyclin E (MRHHHHHHK)-(29E-395A)-(SAWRHPQFGG) (SEQ. ID. NO. 7)/cdk2 complexes are active. The kinase activity of the cyclin E (MRHHHHHHK)-(29E-395A)-(SAWRHPQFGG) (SEQ. ID. NO. 7)/cdk2 complex can be further stimulated by the presence of a cyclin-dependent activating kinase (CAK).

In addition, the C-terminal strep tag may also be used for binding to immobilized streptavidin and further purification of the soluble (MRHHHHHHK)-(29E-395A)-(SAWRHPQFGG) (SEQ. ID. NO. 7)/cdk2. This is also important because it would allow the complex to be used in assays requiring binding to streptavidin, for example, in Scintillation Proximity Assay (SPA) based on streptavidin-coated beads.

Assays Using Special Cyclin E/cdk2 Complexes for Detecting Interaction with Kinase Inhibitor Proteins (KIPs)

The present invention includes the use of either GST-cyclin E-PEST*-His6/cdk2 complexes or cyclin E (MRHHHHHHK)-(29E-395A)-(SAWRHPQFGG) (SEQ. ID. NO. 7)/cdk2 complexes in a scintillation proximity assay that detects their association with members of the p21/p27 family of Kinase Inhibitor Proteins (KIPs). Complexes are biotinylated and then are adsorbed to streptavidin-coated SPA beads. Radiolabeled KIP molecules are then added, and association with the special cyclin E/cdk2-SPA bead complexes induce scintillation. As an alternative to biotinylation, specific antibodies may be used to attach the special cyclin E/cdk2 complexes to SPA beads. As another alternative to biotinylation, the strep-tag on cyclin E (MRHHHHHHK)-(29E-395A)-(SAWRHPQFGG) (SEQ. ID. NO. 7)/cdk2 may be utilized in conjunction with streptavidin-coated SPA beads. A schematic representation of a strep tag approach for a SPA-based KIP assay for screening Kip mimetics is shown in FIG. 15. The strep tag is engineered to the C-terminus of a truncated version (29E-395A) of human cyclin E which is then complexed with recombinant cdk2. This complex binds to streptavidin coated SPA beads by virtue of the presence of the strep tag at the C-terminus of human cyclin E. For the experiment shown in FIG. 15, the minimal domain (amino acids 28 to 81) of the kinase inhibitory protein (Kip) p27, expressed as ubiquitin fusion in E. coli, is used and referred to as "mini p27."

A dose-response study (FIG. 16) showed that the special cyclin E (MRHHHHHHK)-(29E-395A)-(SAWRHPQFGG) (SEQ. ID. NO. 7)/cdk2 complexes are approaching saturation with mini p27 (200 nM) at about 200 nM of the complex. The specificity of this assay is demonstrated by displacement of the [$^3$H] labeled mini p27 in the presence of cold mini p27. Almost complete displacement of the labeled protein is observed at about 2.0 uM of the competing mini p27. Similar results have been obtained using biotinylated GST-cyclin E-PEST*-His6/cdk2 complexes (FIG. 6). Recombinant cdk2 alone, or a human cyclin E/cdk2 complexes incapable of adsorption to SPA beads are used as negative controls and showed no SPA counts.

As described in Rogers et al., Science 234, 364–368 (1986), the PEST motif is a domain rich in proline (P), glutamic acid (E), serine (S) and threonine (T).

I claim:

1. A polypeptide, comprising the amino acid sequence of SEQ. ID. NO. 2.

2. A composition comprising the polypeptide of of SEQ. ID. NO. 2 bound to Cdk2.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1951 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:1:

```
ATGTCCCCTA TACTAGGTTA TTGGAAAATT AAGGGCCTTG TGCAACCCAC TCGACTTCTT      60

TTGGAATATC TTGAAGAAAA ATATGAAGAG CATTTGTATG AGCGCGATGA AGGTGATAAA     120

TGGCGAAACA AAAAGTTTGA ATTGGGTTTG GAGTTTCCCA ATCTTCCTTA TTATATTGAT     180

GGTGATGTTA AATTAACACA GTCTATGGCC ATCATACGTT ATATAGCTGA CAAGCACAAC     240

ATGTTGGGTG GTTGTCCAAA AGAGCGTGCA GAGATTTCAA TGCTTGAAGG AGCGGTTTTG     300

GATATTAGAT ACGGTGTTTC GAGAATTGCA TATAGTAAAG ACTTTGAAAC TCTCAAAGTT     360

GATTTTCTTA GCAAGCTACC TGAAATGCTG AAAATGTTCG AAGATCGTTT ATGTCATAAA     420

ACATATTTAA ATGGTGATCA TGTAACCCAT CCTGACTTCA TGTTGTATGA CGCTCTTGAT     480

GTTGTTTTAT ACATGGACCC AATGTGCCTG GATGCGTTCC CAAAATTAGT TTGTTTTAAA     540

AAACGTATTG AAGCTATCCC ACAAATTGAT AAGTACTTGA AATCCAGCAA GTATATAGCA     600

TGGCCTTTGC AGGGCTGGCA AGCCACGTTT GGTGGTGTCG ACCATCCTCC AAAATCGGAT     660

CTCATGAAGG AGGACGGCGG CGCGGAGTTC TCGGCTCGCT CCAGGAAGAG GAAGGCAAAC     720

GTGACCGTTT TTTTGCAGGA TCCAGATGAA GAAATGGCCA AATCGACAG GACGGCGAGG      780

GACCAGTGTG GGAGCCAGCC TTGGGACAAT AATGCAGTCT GTGCAGACCC CTGCTCCCTG     840
```

```
ATCCCCACAC CTGACAAAGA AGATGATGAC CGGGTTTACC CAAACTCAAC GTGCAAGCCT   900

CGGATTATTG CACCATCCAG AGGCTCCCCG CTGCCTGTAC TGAGCTGGGC AAATAGAGAG   960

GAAGTCTGGA AAATCATGTT AAACAAGGAA AAGCATACAT TAAGGGATCA GCACTTTCTT  1020

GAGCAACACC CTCTTCTGCA GCCAAAAATG CGAGCAATTC TTCTGGATTG GTTAATGGAG  1080

GTGTGTGAAG TCTATAAACT TCACAGGGAG ACCTTTTACT TGGCACAAGA TTTCTTTGAC  1140

CGGTATATGG CGACACAAGA AAATGTTGTA AAAACTCTTT TACAGCTTAT TGGGATTTCA  1200

TCTTTATTTA TTGCAGCCAA ACTTGAGGAA ATCTATCCTC AAAGTTGCA CCAGTTTGCG  1260

TATGTGACAG ATGGAGCTTG TTCAGGAGAT GAAATTCTCA CCATGGAATT AATGATTATG  1320

AAGGCCCTTA AGTGGCGTTT AAGTCCCCTG ACTATTGTGT CCTGGCTGAA TGTATACATG  1380

CAGGTTGCAT ATCTAAATGA CTTACATGAA GTGCTACTGC CGCAGTATCC CCAGCAAATC  1440

TTTATACAGA TTGCAGAGCT GTTGGATCTC TGTGTCCTGG ATGTTGACTG CCTTGAATTT  1500

CTTACATGAA GTGCTACTGC CGCAGTATCC CCAGCAAATC TTTATACAGA TTGCAGAGCT  1560

GTTGGATCTC TGTGTCCTGG ATGTTGACTG CCTTGAATTT CCTTATGGTA TACTTGCTGC  1620

TTCGGCCTTG TATCATTTCT CGTCATCTGA ATTGATGCAA AAGGTTTCAG GGTATCAGTG  1680

GTGCGACATA GAGAACTGTG TCAAGTGGAT GGTTCCATTT GCCATGGTTA TAAGGGAGAC  1740

GGGGAGCTCA AAACTGAAGC ACTTCAGGGG CGTCGCTGAT GAAGATGCAC ACAACATACA  1800

GACCCACAGA GACAGCTTGG ATTTGCTGGA CAAAGCCCGA GCAAAGAAAG CCATGTTGTC  1860

TGAACAAAAT AGGGCTTCTC CTCTCCCCAG TGGGCTCCTC ATCGCGGCAC AGGGCGGTAA  1920

GAAGCAGAGC CACCACCACC ACCACCACTG A                                1951
```

(2) INFORMATION FOR SEQ ID NO:2:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:2:

```
Met Ser Pro Ile Leu Gly Tyr Trp Lys Ile Lys Gly Leu Val Gln Pro
1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
```

```
                115                 120                 125
Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Val Asp His Pro Pro Lys Ser Asp Leu Met Lys Glu
    210                 215                 220

Asp Gly Gly Ala Glu Phe Ser Ala Arg Ser Arg Lys Arg Lys Ala Asn
225                 230                 235                 240

Val Thr Val Phe Leu Gln Asp Pro Asp Glu Met Ala Lys Ile Asp
                245                 250                 255

Arg Thr Ala Arg Asp Gln Cys Gly Ser Gln Pro Trp Asp Asn Asn Ala
            260                 265                 270

Val Cys Ala Asp Pro Cys Ser Leu Ile Pro Thr Pro Asp Lys Glu Asp
        275                 280                 285

Asp Asp Arg Val Tyr Pro Asn Ser Thr Cys Lys Pro Arg Ile Ile Ala
    290                 295                 300

Pro Ser Arg Gly Ser Pro Leu Pro Val Leu Ser Trp Ala Asn Arg Glu
305                 310                 315                 320

Glu Val Trp Lys Ile Met Leu Asn Lys Glu Lys Thr Tyr Leu Arg Asp
                325                 330                 335

Gln His Phe Leu Glu Gln His Pro Leu Leu Gln Pro Lys Met Arg Ala
            340                 345                 350

Ile Leu Leu Asp Trp Leu Met Glu Val Cys Glu Val Tyr Lys Leu His
        355                 360                 365

Arg Glu Thr Phe Tyr Leu Ala Gln Asp Phe Phe Asp Arg Tyr Met Ala
    370                 375                 380

Thr Gln Glu Asn Val Val Lys Thr Leu Leu Gln Leu Ile Gly Ile Ser
385                 390                 395                 400

Ser Leu Phe Ile Ala Ala Lys Leu Glu Glu Ile Tyr Pro Pro Lys Leu
                405                 410                 415

His Gln Phe Ala Tyr Val Thr Asp Gly Ala Cys Ser Gly Asp Glu Ile
            420                 425                 430

Leu Thr Met Glu Leu Met Ile Met Lys Ala Leu Lys Trp Arg Leu Ser
        435                 440                 445

Pro Leu Thr Ile Val Ser Trp Leu Asn Val Tyr Met Gln Val Ala Tyr
    450                 455                 460

Leu Asn Asp Leu His Glu Val Leu Leu Pro Gln Tyr Pro Gln Gln Ile
465                 470                 475                 480

Phe Ile Gln Ile Ala Glu Leu Leu Asp Leu Cys Val Leu Asp Val Asp
                485                 490                 495

Cys Leu Glu Phe Pro Tyr Gly Ile Leu Ala Ala Ser Ala Leu Tyr His
            500                 505                 510

Phe Ser Ser Ser Glu Leu Met Gln Lys Val Ser Gly Tyr Gln Trp Cys
        515                 520                 525

Asp Ile Glu Asn Cys Val Lys Trp Met Val Pro Phe Ala Met Val Ile
    530                 535                 540
```

```
Arg Glu Thr Gly Ser Ser Lys Leu Lys His Phe Arg Gly Val Ala Asp
545                 550                 555                 560

Glu Asp Ala His Asn Ile Gln Thr His Arg Asp Ser Leu Asp Leu Leu
                565                 570                 575

Asp Lys Ala Arg Ala Lys Lys Ala Met Leu Ser Glu Gln Asn Arg Ala
            580                 585                 590

Ser Pro Leu Pro Ser Gly Leu Leu Ile Ala Ala Gln Gly Gly Lys Lys
            595                 600                 605

Gln Ser His His His His His His
    610                 615
```

(2) INFORMATION FOR SEQ ID NO:3:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:3:

```
Arg Ala Ser Pro Leu Pro Ser Gly Leu Leu Thr Pro Pro Gln Ser Gly
1               5                   10                  15

Lys Lys Gln Ser Ser Gly Pro Glu Met Ala
            20                  25
```

(2) INFORMATION FOR SEQ ID NO:4:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:4:

```
AGGGCTTCTC CTCTCCCCAG TGGGCTCCTC ACCCCGCCAC AGAGCGGTAA GAAGCAGAGC      60

AGCGGGCCGG AAATGGCGTG A                                               81
```

(2) INFORMATION FOR SEQ ID NO:5:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:5:

| | | | | | |
|---|---|---|---|---|---|
| GAAGAAATGG | CCAAAATCGA | CAGGACGGCG | AGGGACCAGT | GTGGGAGCCA | GCCTTGGGAC | 60 |
| AATAATGCAG | TCTGTGCAGA | CCCCTGCTCC | CTGATCCCCA | CACCTGACAA | AGAAGATGAT | 120 |
| GACCGGGTTT | ACCCAAACTC | AACGTGCAAG | CCTCGGATTA | TTGCACCATC | CAGAGGCTCC | 180 |
| CCGCTGCCTG | TACTGAGCTG | GCAAATAGA | GAGGAAGTCT | GGAAAATCAT | GTTAAACAAG | 240 |
| GAAAAGACAT | ACTTAAGGGA | TCAGCACTTT | CTTGAGCAAC | ACCCTCTTCT | GCAGCCAAAA | 300 |
| ATGCGAGCAA | TTCTTCTGGA | TTGGTTAATG | GAGGTGTGTG | AAGTCTATAA | ACTTCACAGG | 360 |
| GAGACCTTTT | ACTTGGCACA | AGATTTCTTT | GACCGGTATA | TGGCGACACA | AGAAAATGTT | 420 |
| GTAAAAACTC | TTTTACAGCT | TATTGGGATT | TCATCTTTAT | TTATTGCAGC | CAAACTTGAG | 480 |
| GAAATCTATC | CTCCAAAGTT | GCACCAGTTT | GCGTATGTGA | CAGATGGAGC | TTGTTCAGGA | 540 |
| GATGAAATTC | TCACCATGGA | ATTAATGATT | ATGAAGGCCC | TTAAGTGGCG | TTTAAGTCCC | 600 |
| CTGACTATTG | TGTCCTGGCT | GAATGTATAC | ATGCAGGTTG | CATATCTAAA | TGACTTACAT | 660 |
| GAAGTGCTAC | TGCCGCAGTA | TCCCCAGCAA | ATCTTTATAC | AGATTGCAGA | GCTGTTGGAT | 720 |
| CTCTGTGTCC | TGGATGTTGA | CTGCCTTGAA | TTTCCTTATG | GTATACTTGC | TGCTTCGGCC | 780 |
| TTGTATCATT | TCTCGTCATC | TGAATTGATG | CAAAAGGTTT | CAGGGTATCA | GTGGTGCGAC | 840 |
| ATAGAGAACT | GTGTCAAGTG | GATGGTTCCA | TTTGCCATGG | TTATAAGGGA | GACGGGGAGC | 900 |
| TCAAAACTGA | AGCACTTCAG | GGGCGTCGCT | GATGAAGATG | CACACAACAT | ACAGACCCAC | 960 |
| AGAGACAGCT | TGGATTTGCT | GGACAAAGCC | CGAGCAAAGA | AAGCCATGTT | GTCTGAACAA | 1020 |
| AATAGGGCTT | CTCCTCTCCC | CAGTGGGCTC | CTCACCCCGC | CACAGAGCGG | TAAGAAGCAG | 1080 |
| AGCAGCGGGC | CGGAAATGGC | G | | | | 1101 |

(2) INFORMATION FOR SEQ ID NO:6:

(i) SEQUENCE CHARACTERISTICS:
        (A) LENGTH: 367 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:6:

```
Glu Glu Met Ala Lys Ile Asp Arg Thr Ala Arg Asp Gln Cys Gly Ser
1               5                   10                  15

Gln Pro Trp Asp Asn Asn Ala Val Cys Ala Asp Pro Cys Ser Leu Ile
            20                  25                  30

Pro Thr Pro Asp Lys Glu Asp Asp Arg Val Tyr Pro Asn Ser Thr
        35                  40                  45

Cys Lys Pro Arg Ile Ile Ala Pro Ser Arg Gly Ser Pro Leu Pro Val
    50                  55                  60

Leu Ser Trp Ala Asn Arg Glu Glu Val Trp Lys Ile Met Leu Asn Lys
65                  70                  75                  80

Glu Lys Thr Tyr Leu Arg Asp Gln His Phe Leu Glu Gln His Pro Leu
                85                  90                  95
```

-continued

```
Leu Gln Pro Lys Met Arg Ala Ile Leu Leu Asp Trp Leu Met Glu Val
            100                 105                 110

Cys Glu Val Tyr Lys Leu His Arg Glu Thr Phe Tyr Leu Ala Gln Asp
        115                 120                 125

Phe Phe Asp Arg Tyr Met Ala Thr Gln Glu Asn Val Val Lys Thr Leu
130                 135                 140

Leu Gln Leu Ile Gly Ile Ser Ser Leu Phe Ile Ala Ala Lys Leu Glu
145                 150                 155                 160

Glu Ile Tyr Pro Pro Lys Leu His Gln Phe Ala Tyr Val Thr Asp Gly
                165                 170                 175

Ala Cys Ser Gly Asp Glu Ile Leu Thr Met Glu Leu Met Ile Met Lys
            180                 185                 190

Ala Leu Lys Trp Arg Leu Ser Pro Leu Thr Ile Val Ser Trp Leu Asn
        195                 200                 205

Val Tyr Met Gln Val Ala Tyr Leu Asn Asp Leu His Glu Val Leu Leu
    210                 215                 220

Pro Gln Tyr Pro Gln Gln Ile Phe Ile Gln Ile Ala Glu Leu Leu Asp
225                 230                 235                 240

Leu Cys Val Leu Asp Val Asp Cys Leu Glu Phe Pro Tyr Gly Ile Leu
                245                 250                 255

Ala Ala Ser Ala Leu Tyr His Phe Ser Ser Ser Glu Leu Met Gln Lys
            260                 265                 270

Val Ser Gly Tyr Gln Trp Cys Asp Ile Glu Asn Cys Val Lys Trp Met
        275                 280                 285

Val Pro Phe Ala Met Val Ile Arg Glu Thr Gly Ser Ser Lys Leu Lys
    290                 295                 300

His Phe Arg Gly Val Ala Asp Glu Asp Ala His Asn Ile Gln Thr His
305                 310                 315                 320

Arg Asp Ser Leu Asp Leu Leu Asp Lys Ala Arg Ala Lys Lys Ala Met
                325                 330                 335

Leu Ser Glu Gln Asn Arg Ala Ser Pro Leu Pro Ser Gly Leu Leu Thr
            340                 345                 350

Pro Pro Gln Ser Gly Lys Lys Gln Ser Ser Gly Pro Glu Met Ala
        355                 360                 365

(2) INFORMATION FOR SEQ ID NO:7:

(i) SEQUENCE CHARACTERISTICS:
        (A) LENGTH: 386 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:7:

Met Arg His His His His His His Lys Glu Glu Met Ala Lys Ile Asp
1               5                   10                  15

Arg Thr Ala Arg Asp Gln Cys Gly Ser Gln Pro Trp Asp Asn Asn Ala
            20                  25                  30

Val Cys Ala Asp Pro Cys Ser Leu Ile Pro Thr Pro Asp Lys Glu Asp
        35                  40                  45
```

Asp Asp Arg Val Tyr Pro Asn Ser Thr Cys Lys Pro Arg Ile Ile Ala
    50                  55                  60

Pro Ser Arg Gly Ser Pro Leu Pro Val Leu Ser Trp Ala Asn Arg Glu
65                  70                  75                  80

Glu Val Trp Lys Ile Met Leu Asn Lys Glu Lys Thr Tyr Leu Arg Asp
                85                  90                  95

Gln His Phe Leu Glu Gln His Pro Leu Leu Gln Pro Lys Met Arg Ala
            100                 105                 110

Ile Leu Leu Asp Trp Leu Met Glu Val Cys Glu Val Tyr Lys Leu His
            115                 120                 125

Arg Glu Thr Phe Tyr Leu Ala Gln Asp Phe Phe Asp Arg Tyr Met Ala
        130                 135                 140

Thr Gln Glu Asn Val Val Lys Thr Leu Leu Gln Leu Ile Gly Ile Ser
145                 150                 155                 160

Ser Leu Phe Ile Ala Ala Lys Leu Glu Glu Ile Tyr Pro Pro Lys Leu
            165                 170                 175

His Gln Phe Ala Tyr Val Thr Asp Gly Ala Cys Ser Gly Asp Glu Ile
            180                 185                 190

Leu Thr Met Glu Leu Met Ile Met Lys Ala Leu Lys Trp Arg Leu Ser
        195                 200                 205

Pro Leu Thr Ile Val Ser Trp Leu Asn Val Tyr Met Gln Val Ala Tyr
        210                 215                 220

Leu Asn Asp Leu His Glu Val Leu Leu Pro Gln Tyr Pro Gln Gln Ile
225                 230                 235                 240

Phe Ile Gln Ile Ala Glu Leu Leu Asp Leu Cys Val Leu Asp Val Asp
            245                 250                 255

Cys Leu Glu Phe Pro Tyr Gly Ile Leu Ala Ala Ser Ala Leu Tyr His
            260                 265                 270

Phe Ser Ser Ser Glu Leu Met Gln Lys Val Ser Gly Tyr Gln Trp Cys
        275                 280                 285

Asp Ile Glu Asn Cys Val Lys Trp Met Val Pro Phe Ala Met Val Ile
        290                 295                 300

Arg Glu Thr Gly Ser Ser Lys Leu Lys His Phe Arg Gly Val Ala Asp
305                 310                 315                 320

Glu Asp Ala His Asn Ile Gln Thr His Arg Asp Ser Leu Asp Leu Leu
            325                 330                 335

Asp Lys Ala Arg Ala Lys Lys Ala Met Leu Ser Glu Gln Asn Arg Ala
            340                 345                 350

Ser Pro Leu Pro Ser Gly Leu Leu Thr Pro Pro Gln Ser Gly Lys Lys
        355                 360                 365

Gln Ser Ser Gly Pro Glu Met Ala Ser Ala Trp Arg His Pro Gln Phe
370                 375                 380

Gly Gly
385

(2) INFORMATION FOR SEQ ID NO:8:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:8:

```
ATGCGACACC ATCACCATCA CCATAAGGAA GAAATGGCCA AAATCGACAG GACGGCGAGG    60
GACCAGTGTG GGAGCCAGCC TTGGGACAAT AATGCAGTCT GTGCAGACCC CTGCTCCCTG   120
ATCCCCACAC CTGACAAAGA AGATGATGAC CGGGTTTACC CAAACTCAAC GTGCAAGCCT   180
CGGATTATTG CACCATCCAG AGGCTCCCCG CTGCCTGTAC TGAGCTGGGC AAATAGAGAG   240
GAAGTCTGGA AAATCATGTT AAACAAGGAA AAGACATACT TAAGGGATCA GCACTTTCTT   300
GAGCAACACC CTCTTCTGCA GCCAAAAATG CGAGCAATTC TTCTGGATTG GTTAATGGAG   360
GTGTGTGAAG TCTATAAACT TCACAGGGAG ACCTTTTACT TGGCACAAGA TTTCTTTGAC   420
CGGTATATGG CGACACAAGA AAATGTTGTA AAAACTCTTT TACAGCTTAT TGGGATTTCA   480
TCTTTATTTA TTGCAGCCAA ACTTGAGGAA ATCTATCCTC CAAAGTTGCA CCAGTTTGCG   540
TATGTGACAG ATGGAGCTTG TTCAGGAGAT GAAATTCTCA CCATGGAATT AATGATTATG   600
AAGGCCCTTA AGTGGCGTTT AAGTCCCCTG ACTATTGTGT CCTGGCTGAA TGTATACATG   660
CAGGTTGCAT ATCTAAATGA CTTACATGAA GTGCTACTGC CGCAGTATCC CCAGCAAATC   720
TTTATACAGA TTGCAGAGCT GTTGGATCTC TGTGTCCTGG ATGTTGACTG CCTTGAATTT   780
CCTTATGGTA TACTTGCTGC TTCGGCCTTG TATCATTTCT CGTCATCTGA ATTGATGCAA   840
AAGGTTTCAG GGTATCAGTG GTGCGACATA GAGAACTGTG TCAAGTGGAT GGTTCCATTT   900
GCCATGGTTA TAAGGGAGAC GGGGAGCTCA AAACTGAAGC ACTTCAGGGG CGTCGCTGAT   960
GAAGATGCAC ACAACATACA GACCCACAGA GACAGCTTGG ATTTGCTGGA CAAAGCCCGA  1020
GCAAAGAAAG CCATGTTGTC TGAACAAAAT AGGGCTTCTC CTCTCCCCAG TGGGCTCCTC  1080
ACCCCGCCAC AGAGCGGTAA GAAGCAGAGC AGCGGGCCGG AAATGGCGAG CGCATGGAGA  1140
CACCCCCAGT TTGGAGGA                                                1158
```

(2) INFORMATION FOR SEQ ID NO:9:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:9:

```
Met Arg His His His His His His Lys
 1               5
```

(2) INFORMATION FOR SEQ ID NO:10:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:10:

ATGCGACACC ATCACCATCA CCATAAG                                              27

(2) INFORMATION FOR SEQ ID NO:11:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:11:

Ser Ala Trp Arg His Pro Gln Phe Gly Gly
1               5                   10

(2) INFORMATION FOR SEQ ID NO:12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:12:

AGCGCATGGA GACACCCCCA GTTTGGAGGA                                           30

(2) INFORMATION FOR SEQ ID NO:13:

(i) SEQUENCE CHARACTERISTICS:
            (A) LENGTH: 67 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:13:

GCAGATCTTC AGTGGTGGTG GTGGTGGTGG CTCTGCTTCT TACCGCCCTG TGCCGCGATG          60

AGGAGCC                                                                   67

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:14:

GATCAGATCT CATGAAGGAG GACGGCGGCG                                          30

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:15:

Met Arg His His His His His His Lys Glu Glu Met Ala Lys Ile Asp
1               5                   10                  15

Arg Thr (2) INFORMATION FOR SEQ ID NO:16:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:16:

GGAATTCCAT ATGCGACACC ATCACCATCA CCATAAGGAA GAAATGGCCA AAATCGACAG         60

GACG                                                                     64

(2) INFORMATION FOR SEQ ID NO:17:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:17:

Gly Gly Phe Gln Pro His Arg Trp Ala Ser Ala Met Glu Pro Gly Ser
1               5                   10                  15

Ser Gln Lys (2) INFORMATION FOR SEQ ID NO:18:

(i) SEQUENCE CHARACTERISTICS:
          (A) LENGTH: 69 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:18:

CCCAAGCTTC TATCCTCCAA ACTGGGGGTG TCTCCATGCG CTCGCCATTT CCGGCCCGCT        60

GCTCTGCTT                                                                69

(2) INFORMATION FOR SEQ ID NO:19:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:19:

ATGAAGGAGG ACGGCGGCG                                                     19

(2) INFORMATION FOR SEQ ID NO:20:

(i) SEQUENCE CHARACTERISTICS:
          (A) LENGTH:  11 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (xi) SEQUENCE DESCRIPTION: SEQ ID NO:20:

GATCAGATCT C                                                             11

(2) INFORMATION FOR SEQ ID NO:21:

(i) SEQUENCE CHARACTERISTICS:

```
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:21:

Arg Ala Ser Pro Leu Pro Ser Gly Leu Leu Ile Ala Ala Gln Gly Gly
1               5                   10                  15

Lys Lys Gln Ser His His His His His
            20                  25
```